United States Patent
Hegazi et al.

(10) Patent No.: US 6,633,043 B2
(45) Date of Patent: Oct. 14, 2003

(54) METHOD FOR CHARACTERIZATION OF PETROLEUM OILS USING NORMALIZED TIME-RESOLVED FLUORESCENCE SPECTRA

(76) Inventors: Ezzat M. Hegazi, Center for Applied Physical Science, Research Institute, King Fahd University of Petroleum and Minerals, Box #5044, Dhahran, 31261 (SA); Abdullah M. Hamdan, Laerholz Strasse, Laerholz 21, App. 309, 44801 Bochum (DE); Joseph N. Mastromarino, Georgia Institute of Technology, Baker Building Room 107, Atlanta, GA (US) 30332

( * ) Notice: Subject to any disclaimer, the term of this patent is extended or adjusted under 35 U.S.C. 154(b) by 23 days.

(21) Appl. No.: 10/059,020

(22) Filed: Jan. 30, 2002

(65) Prior Publication Data

US 2003/0141459 A1 Jul. 31, 2003

(51) Int. Cl.[7] .............................................. G01N 21/64
(52) U.S. Cl. ................................ 250/461.1; 250/458.1
(58) Field of Search ......................... 250/461.1, 458.1, 250/459.1

(56) References Cited

U.S. PATENT DOCUMENTS

| | | |
|---|---|---|
| 5,049,738 A | 9/1991 | Gergely et al. |
| 5,565,982 A | 10/1996 | Lee et al. |
| 5,656,810 A | 8/1997 | Alfano et al. |
| 5,780,850 A | 7/1998 | DeLaune et al. |
| 6,140,048 A | 10/2000 | Müller et al. |
| 6,268,603 B1 | 7/2001 | Mullins et al. |

OTHER PUBLICATIONS

Measures et al. "Laser Induced Fluorescent Decay Spectra, A New Form of Environmental Signature." Optical Engineering, vol. 13 pp. 494–501 (1974).

Camagni et al. "Diagnostics of Oil Pollution by Laser Induced Fluorescence." IEEE Transactions on Geoscience and Remote Sensing, vol. GE–26, No. 1, pp. 22–26 (1988).

Camagni et al. "Fluorescence Response of Mineral Oils: Spectra Yield vs Absorption and Decay Time." Applied Optics, vol. 30, No. 1, pp. 26–35 (1991).

Quinn et al. Measurement and Analysis Procedures for Remote Identification of Oil Spills Using a Laser Fluorosensor. Journal of International Remote Sensing, vol. 15 pp. 2637–2658 (1994).

Hegazi et al. "New Approach for Spectral Characterization of Crude Oil Using Time–Resolved Fluorescence Spectra." Applied Spectroscopy, vol. 52 pp. 202–207 (2001).

Hegazi et al. Estimation of Crude Oils grade Using Time Resolved Fluorescence Spectra) (Accepted for publication 2002).

*Primary Examiner*—Diego Gutierrez
*Assistant Examiner*—Tania C. Courson
(74) *Attorney, Agent, or Firm*—Richard C. Litman

(57) ABSTRACT

A method based on time-resolved, laser-induced fluorescence spectroscopy for the characterization and fingerprinting of petroleum oils and other complex mixtures. The method depends on exciting the wavelength-resolved fluorescence spectra of samples using ultraviolet pulsed laser radiation, measuring them at specific time gates within the temporal response of the excitation laser pulse, and comparing them in terms of their shapes alone without taking into account their relative intensities. The method provides fingerprints of crude oils without resorting to any kind of approximation, for distinguishing between closely similar crude oils of the same grade, and is useful in remote and non-remote setups, along with applications in fingerprinting blended and non-blended crude oils using different ultraviolet excitation wavelengths. Applications include estimating $_o$API gravity of crude oils and monitoring degradation of mineral oils.

20 Claims, 18 Drawing Sheets

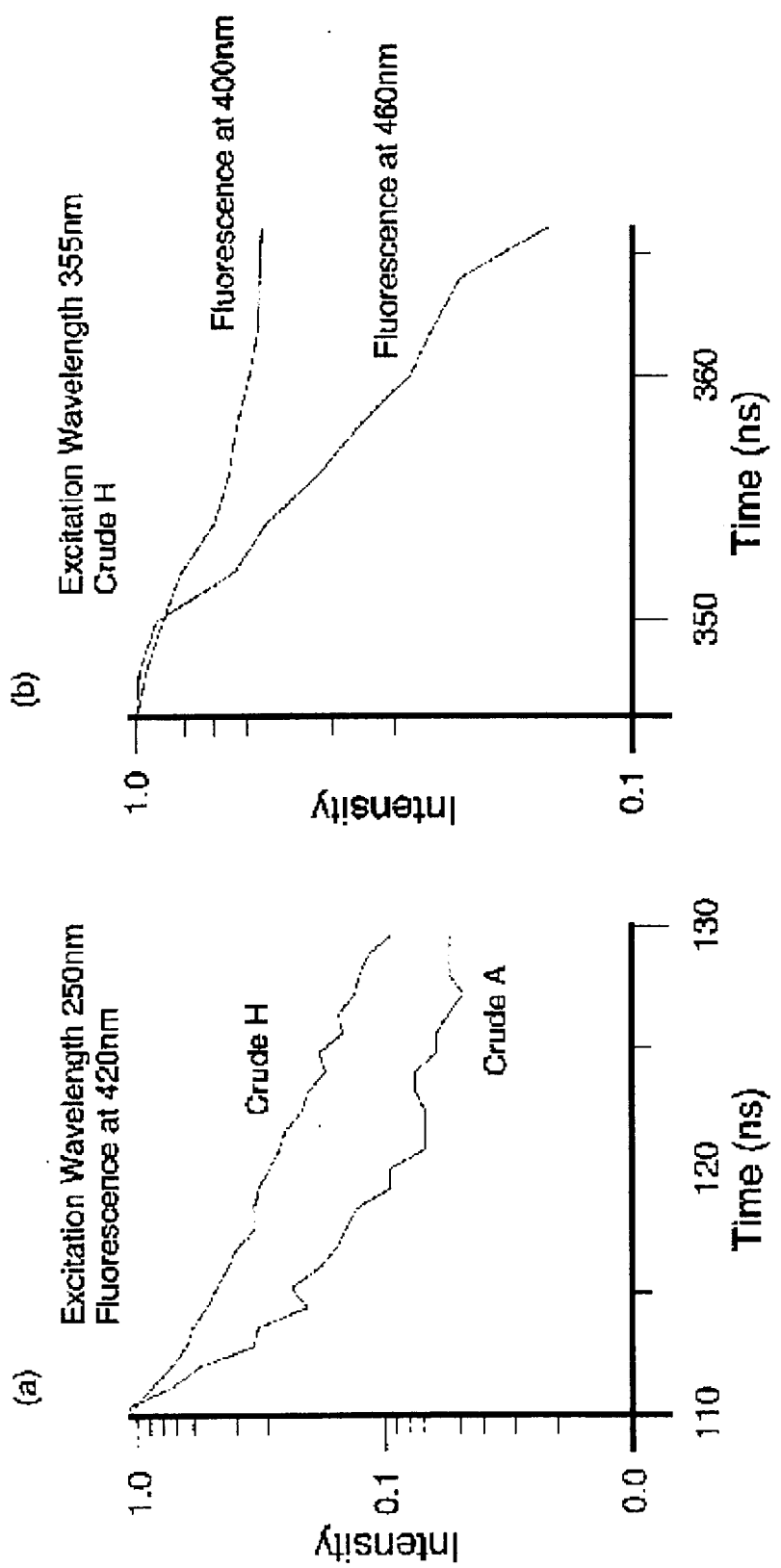

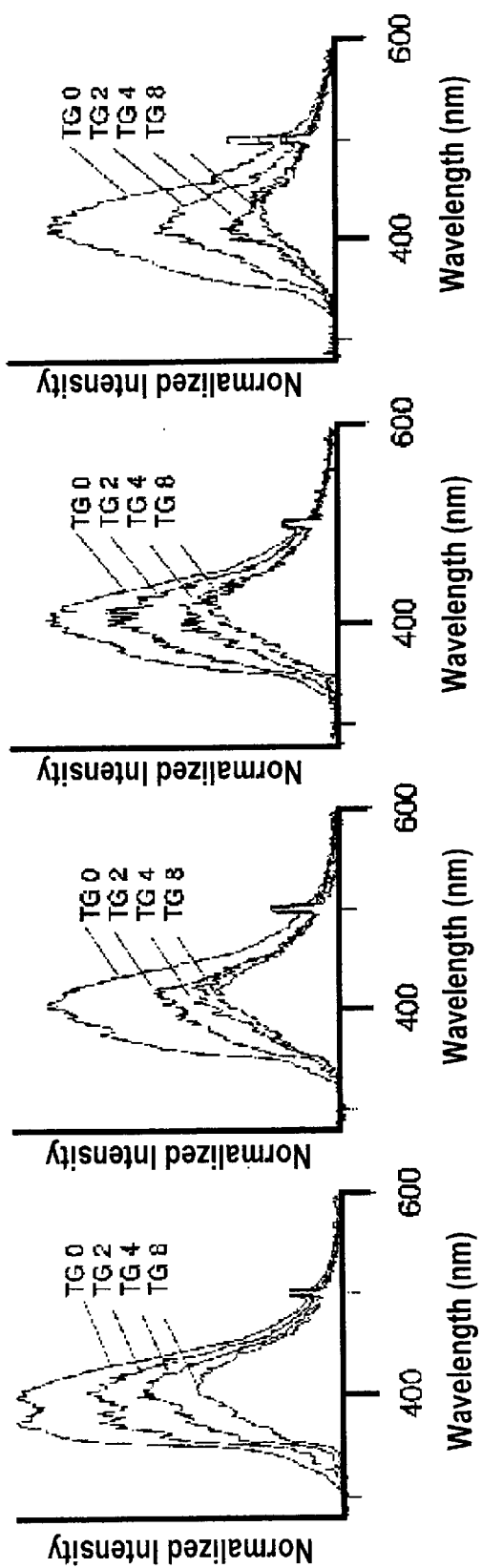

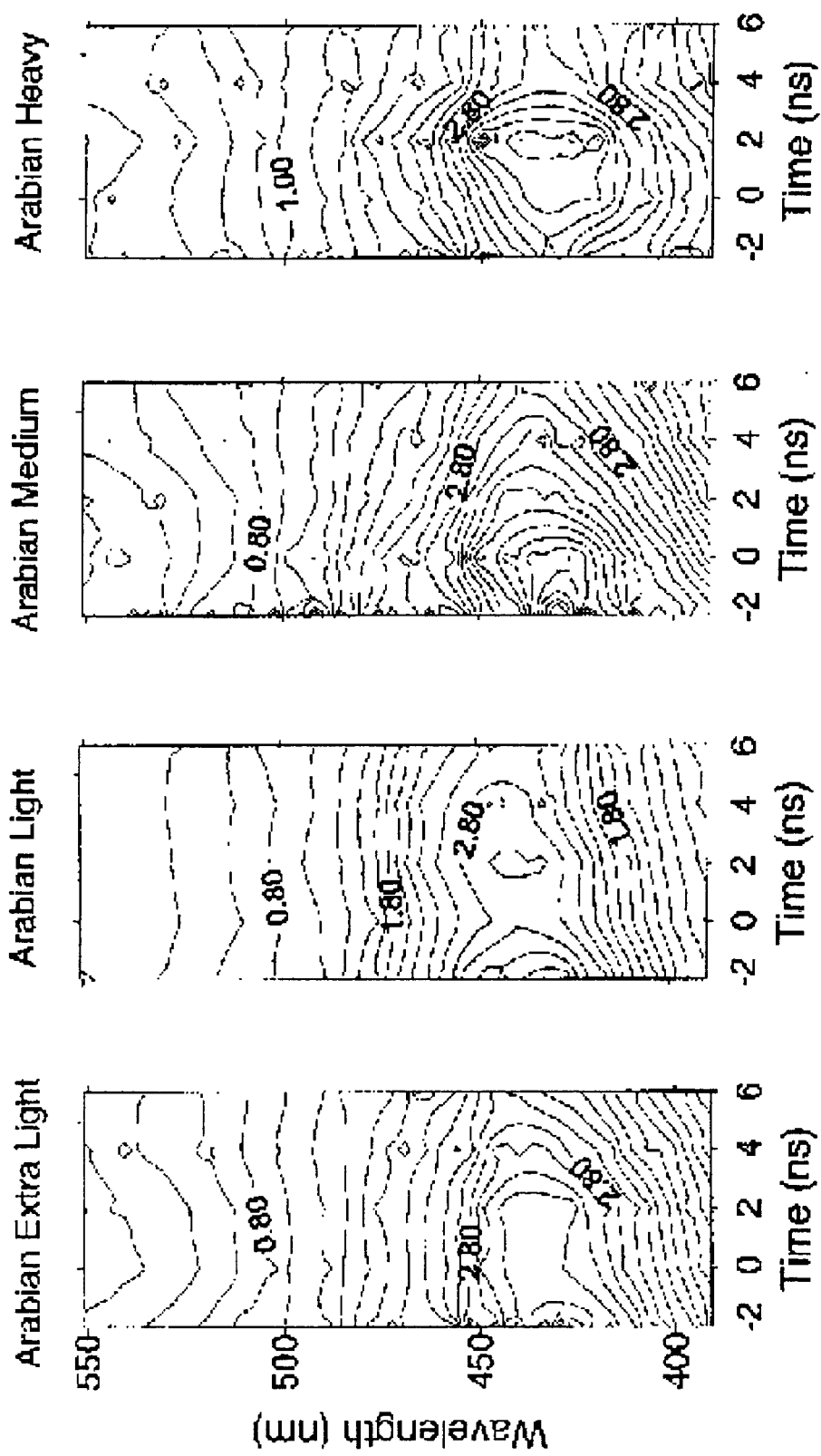

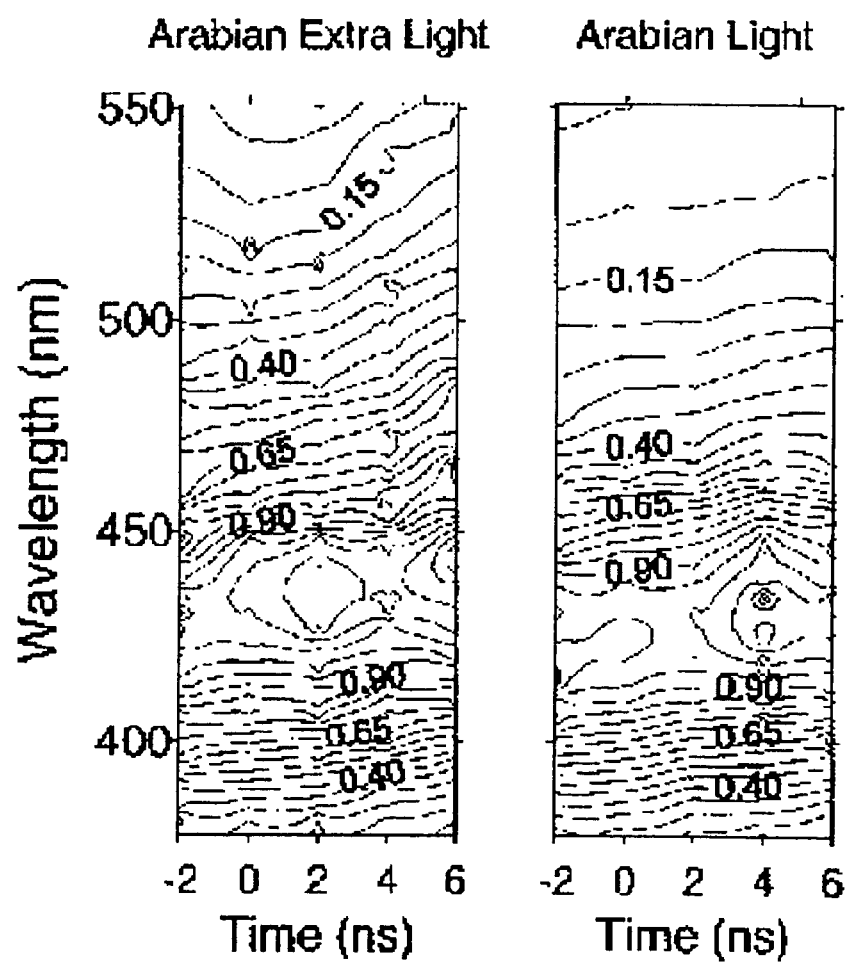
*Fig. 15A*  *Fig. 15B*

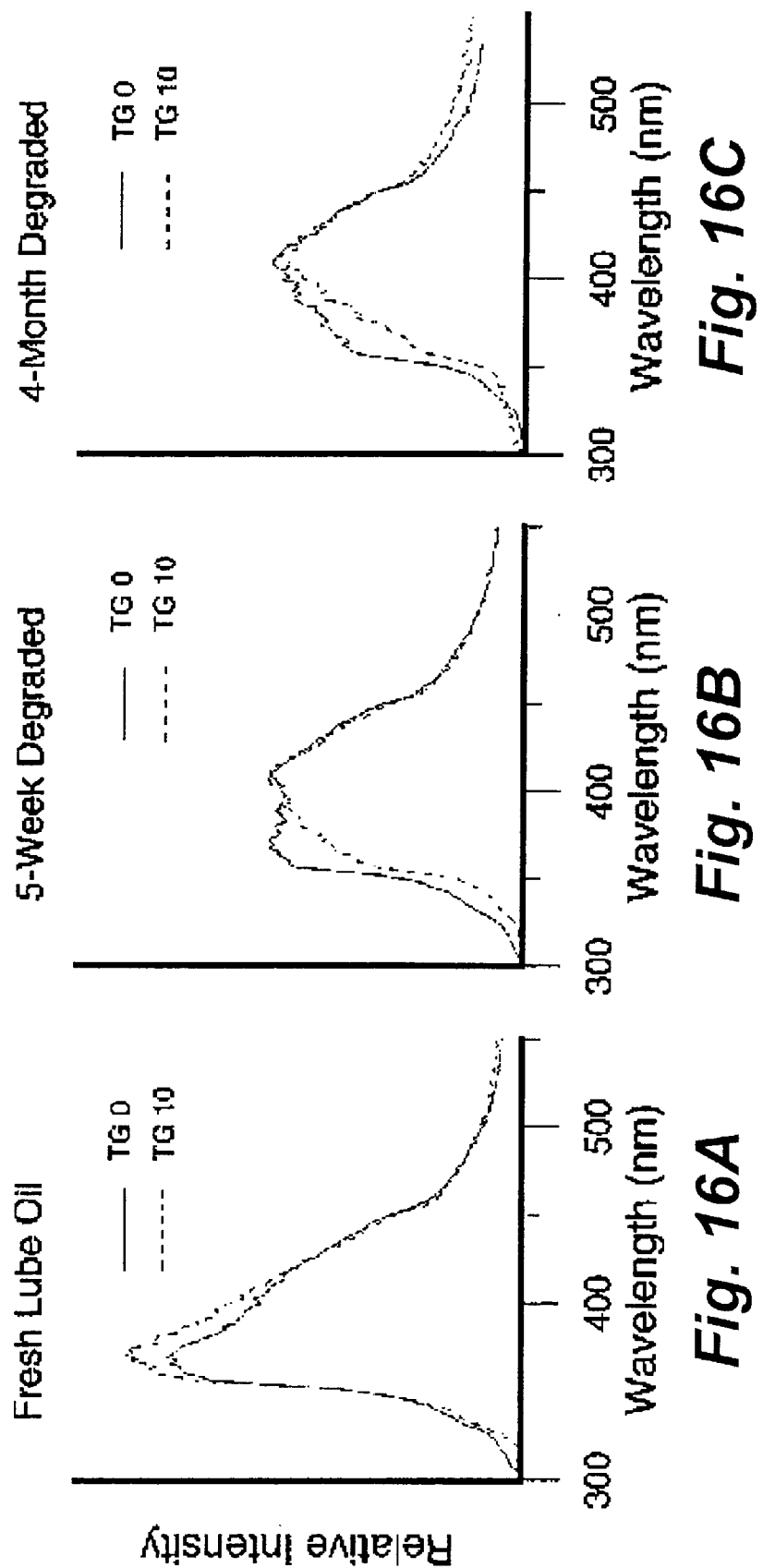

METHOD FOR CHARACTERIZATION OF PETROLEUM OILS USING NORMALIZED TIME-RESOLVED FLUORESCENCE SPECTRA

BACKGROUND OF THE INVENTION

1. Field of the Invention

The present invention relates to spectroscopy. More particularly, the present invention relates to the spectral characterization of crude oil using time-resolved laser-induced fluorescence spectroscopy.

2. Description of the Related Art

Characterization of petroleum oil is customarily made using a number of analytical methods that investigate its physical and chemical properties(See Ali. "Full Range Crudes, Analytical Methodology of." in Encyclopedia of Analytical Chemistry. R. A. Meyers (Ed.) pp. 6709–6726. John Wiley & Sons Ltd, Chichester, 2000)). These methods, which have been standardized comprehensively by ASTM, aim at identifying a number of characteristics such as density, thermal stability, heavy-metal contents, types and quantities of the hydrocarbon groups, types and quantities of the aliphatic and aromatic compounds, etc., which collectively can provide complete sets of data useful in characterizing the petroleum oil. However, because all of these analytical methods require sample preparation, they cannot be used in situations where instant and/or remote characterization is needed. In such cases the laser-induced fluorescence methods would be more suitable. These latter methods give information about the oils by investigating their broad emission spectra when they are excited at specific wavelengths.

The resulting broad emission spectra are due to hundreds of different compounds comprising the oils, which fluoresce with effective lifetimes ranging from a few picoseconds to a few tens of nanoseconds. To get laser-induced fluorescence spectra that are as useful as possible in the characterization process, the excitation wavelength should be in the UV region so that the produced spectra will include contributions from the light aromatic compounds, which usually provide important features along the short wavelength end of the spectra.

The usefulness of these laser-induced fluorescence methods as characterization methods depends largely on the type of the technique employed. There are several of these techniques whose characterization abilities range from merely detecting the presence of oil, as a pollutant for example, to actually distinguishing the different types of oils from each other(See Eastwood. Modern Fluorescence Spectroscopy, V 4 Wehry, Plenum and references therein (1981)). The simplest of these methods is an approved method by both the American Society of testing and materials (ASTM) (See ASTM Book of Standards (1978), p. 720, D3650–78) and the US Coast Guard(See Oil Spill Identification System, Chemistry Branch, U.S. Coast Guard R&D Center, Report No. DOT-CG-D-52-77 (June 1977)3, and it relies on recording the wavelength-resolved fluorescence spectra while exciting the oil with a single UV radiation at 254 nm.

This method can, in principle, be applied in remote sensing, but the information derived from it will allow the distinguishing between only the broad classes of oils, e.g., between light refined oil, crude oil, and heavy residual oil, and not between different grades of oils belonging to the same broad class, e.g., between Light crude oil and Medium crude oil. To do so other fluorescence techniques such as the synchronous scan fluorescence spectroscopy, contour(total luminescence) spectroscopy, or time-resolved fluorescence spectroscopy should be employed.

The synchronous scan fluorescence spectroscopy technique produces spectra resulting from scanning both the excitation wavelength and the detection wavelength with a fixed wavelength separation. By using this technique(See Lloyd. "The nature and evidential value of the luminescence of automobile engine oils and related materials. Part I. Synchronous excitation of fluorescence emission." Journal of Forensic Science Society, vol. 11, pp. 83–94 (1971); Lloyd. "The nature and evidential value of the luminescence of automobile engine oils and related materials. Part III. Separated Luminescence." Journal of Forensic Science Society. Vol. 11, pp. 235–253 (1971); Lloyd. "The nature and evidential value of the luminescence of automobile engine oils and related materials. Part II. Aggregate Luminescence." Journal of Forensic Science Society. Vol. 11, pp. 153–170 (1971); Lloyd "Partly Quenched, Synchronously Excited Fluorescence Emission Spectra in the Characterization of Complex Mixtures." Analyst vol. 99, pp. 729–738 (1974); and Vo-Dinh, et al. "Polynuclear Aromatic Hydrocarbons", $3^{rd}$ International Symposium of Chemical Biology—Carcinogens and Mutagens, p. 111 (1978)) it is possible to distinguish oils belonging to the same broad class from each other, e.g., Light crude oil from Heavy crude oil, but the distinguishing ability is still not adequate enough to discriminate between crude oils of closer grades, such as Medium crude oil and Heavy crude oil(See Shen, et al. "Identification of spilled crude oils from similar Origins." Arabian Journal of Science and Engineering, vol. 10, p. 63 (1984)). In addition, this technique cannot be practically used in remote sensing since it is not easy to tune a high-intensity laser over a wide range of excitation wavelengths.

The contour (total luminescence) spectroscopy technique (See Hornig, Proceedings, Pattern Recognition Applied to Oil Identification, Coronado, Calif. (1976); Warner et al. "Analysis of Multicomponent Fluorescence Data." Analytical Chemistry, vol. 49, p. 564–573 (1977); and Giering et al. "Total Luminescence Spectroscopy, A powerful technique for mixture analysis." American Laboratory, vol. 9 No. 11, pp. 113–123 (1977)) is another technique that can be used for the purpose of crude oil characterization. It produces contour diagrams of oils that are constructed out of many emission spectra each of which is excited at a different wavelength.

This method has a good distinguishing ability between oils belonging to the same broad class, but it is not a method that can be applied practically in remote sensing studies either for the same reason as that mentioned above for the synchronous scan fluorescence technique.

The laser-induced fluorescence technique that promises a good distinguishing ability and, at the same time, a practical remote sensing application is the time-resolved laser-induced fluorescence, technique. The suggestion of this technique as a tool for oil characterization was made as early as 1971 by Fantasia et al(See J. F. Fantasia, T. M. Hard, and H. C. Ingrao. Report No. DOT-TSC-USCG-71-7, Transportation Systems Center, Dept. of Transportation, Cambridge, Mass. (1971) and J. F. Fantasia and H. C. Ingrao. Proc. Of the $9^{th}$ Intern. Symp. On Remote sensing of the environment, Ann Arbor, Mich., Apr. 15–19, 1974, Paper 10700-1-X, 1711–1745)), who recommend the use of lifetime measurements as an additional tool for crude oil characterization.

Immediately thereafter, Measures et al(See Measures et al., "Laser Induced Fluorescent Decay Spectra, A New Form of Environmental Signature." Optical Engineering, vol. 13 pp. 494–501 (1974) and Measures et al. "Laser Induced Spectral Signatures of Relevance to Environmental Sensing." Canadian Journal of Remote Sensing, vol. 1, No. 2, pp. 95–102 (1975)) conducted experiments to study the variation of the fluorescence decay time as a function of wavelength across the emission profile for a variety of materials.

They concluded that, in the case of a complex mixture of molecules, this variation could be used to discriminate between very similar substances, i.e., it could be used as a tool for true fingerprinting. Camagni et al(See Camagni et al. "Diagnostics of Oil Pollution by Laser Induced Fluorescence." IEEE Transactions on Geoscience and Remote Sensing, vol. GE-26, No. 1, pp. 22–26 (1988) and Camagni et al. "Fluorescence Response of Mineral Oils: Spectral Yield vs Absorption and Decay Time." Applied Optics, vol. 30, No. 1, pp. 26–35 (1991)) did one of the early applications of this technique in remote sensing in the mid 1980's. They used a pulsed laser of 4-ns pulse width to excite the fluorescence spectra of crude oils and then aimed at drawing a relation between the temporal decay behaviors measured at different wavelengths to the type of commercial crude oils they studied. Instead of directly de-convolving the instrumental response from the resulting temporal decay curves, which is not usually feasible in remote sensing, they resorted to submitting their data to some regression analysis so as to check the existence of a good deterministic power-law correlation among the different decay curves, which can be considered as the convolution of the instrumental response. Using the following relationship:

$$Y_\lambda(t) = a \cdot [X_\lambda^*(t)]^b$$

(where $Y_\lambda(t)$ represents the observed time response of oil Y at wavelength $\lambda$, $[X_\lambda^*(t)]$ is the observed time response of an arbitrary sample of known exponential behavior, and a and b are the regression parameters), they found that the two quantities characterizing the individual samples namely; average decay time $\tau_\lambda$, and relative efficiency $\rho_\lambda$, become directly related to the regression parameters a and b. Their work showed that these two, quantities could be used meaningfully in the identification off various commercial crude oils.

The work of Camagni et al. represents an application of the time-resolved fluorescence technique to identify crude oils remotely by looking at both the temporal and the spectral characteristics of oils. There are other workers such as Diebel eti al. (See D. Diebel, T. Hengstermann, and R. Reuter, in Remote sensing of pollution of the sea, edited by R. Reuter and R. H. Gillot (Oldenborg: Commission of the European Communities Joint Research Center, ISPRA Establishment and BIS Universitat), SPI 87.46, pp. 266–280 and Diebel et al. Proceedings of an international meeting of the institute of petroleum, London May 1988 (Chichester: John Wiley and Sons), pp. 127–142., Koechler et al(See Koechler et al. Proceedings of S.P.I.E. Conference on Lidar for remote sensing, Berlin, Federal Republic of Germany, 1992 (Bellingham, Wash.: International Society for Optical Engineering), pp. 93–107)), Quinn et al. (See Quinn et al. "Measurement and Analysis Procedures for Remote Identification of Oil Spills Using a Laser Fluorosensor. Journal of International Remote Sensing, vol. 15 pp. 2637–2658 (1994)) and others who also applied similar techniques for the same purposes. The method of '810 does not utilize the time-resolved fluorescence technique.

The availability of streak cameras and other gated CCD devices provides the user of the time-resolved fluorescence technique with the advantage of having instant images of the overall fluorescence intensities as functions of both time and wavelength to be further processed. These digitized images, however, have the instrument response embedded in them, and hence, they still need further de-convolution procedures to extract the wavelength-dependent parameters characterizing the oils, such as the average decay times and the relative efficiencies of the observed fluorescence. This additional de-convolution step is problematic in practice, especially if the identification of oils is to be done remotely, and it also adds to the uncertainty of the results especially when some sort of approximation is needed to determine it.

It would be desirable to provide a simple, readily followed method for characterization of petroleum oils which avoids the pitfalls and complexities of prior characterization methods discussed above.

U.S. Pat. No. 5,656,810, issued Aug. 12, 1997, to Alfano et al., describes a method for evaluating a crude oil sample using spectral differences in the luminescence, excitation, light scattering, and absorption spectra in the near UV, visible, and near IR regions for various crude oils. In one preferred embodiment, the method comprises illuminating an oil sample with light of a suitable excitation wavelength, measuring the resultant fluorescence therefrom, and comparing the resultant fluorescence to appropriate standards derived from known components of crude oil.

The absorption spectra from 190 nm to 2000 nm for the samples show differences. The deasphalted oil sample appears to show less absorption and saturates in the visible spectrum below about 600 nm. Specific examples use excitation wavelengths of 300 nm, 350 nm, 400 nm, and 450 nm.

U.S. Pat. No. 6,140,048, issued Oct. 31, 2000, to Müller et al. describes a system and method for distinguishing at least two types of molecule groups by time resolved fluorescence measurements. Light sources used for exciting the molecules have an emission wavelength of about 600 nm to 900 nm. The method of the '048 patent does not employ the shapes of the time-resolved spectra.

U.S. Pat. No. 5,565,982, issued Oct. 15, 1996, to Lee et al., describes an apparatus and a method for time resolved spectroscopy using pseudo-random modulated diode lasers.

U.S. Pat. No. 5,049,738, issued Jun. 4, 1991, to Gergely, et al., describes a method and apparatus for precise oil correlation using oil-filled fluid inclusions to form signature plots of fluorescence excitation versus emission versus intensity.

U.S. Pat. No. 5,780,850, issued Jul. 14, 1998, to DeLaune, et al., describes a method for evaluating the oAPI gravity of a sample of underground formation including measuring the emission fluorescence of a solvated sample at a fixed excitation wavelength with measurements of emission intensities at two points and characterizing the oil by the ratio of two emission intensities obtained at a fixed excitation wavelength, determining the yield, and applying regression analysis to a data base of oils to obtain an equation which results in an algorithm value, and interpreting the value of the algorithm to give a value for oAPI gravity and estimate in-situ oil concentration.

U.S. Pat. No. 6,268,603, issued Jul. 31, 2001, to Mullins et al., describes methods and apparatuses for investigating formation surrounding a borehole by acquiring a fluorescent signal over the borehole and analyzing the signal to detect the presence of crude oil and to characterize the crude oil.

The present invention deals with oil identification and/or characterization using the time-resolved fluorescence technique also, but it employs a different way of presenting the temporal spectral characteristics of oils. Instead of measuring lifetimes as functions of wavelength, it measures the variations in the spectral profiles of the emitted fluorescence spectra as functions of time(See Hegazi et al. "New Approach for Spectral Characterization of Crude Oil Using Time-Resolved Fluorescence Spectra." Applied Spectroscopy, vol. 52 pp. 202–207 (2001), hereby incorporated by reference.

The technique depends on producing contour diagrams of the fluorescence intensities as functions of time and wavelength simultaneously, which resemble the sort of digital image produced by streak cameras and other gated CCD devices. The difference between them, however, is that these contour diagrams are constructed out of the time-resolved spectra that have been normalized in intensity at a certain particular emission wavelength, and therefore they will show contours representing the "shapes" of the time-resolved spectra alone with no consideration given to their "relative intensities" as in the case of the streak, cameras and the other gated CCD devices. In other words, these diagrams will not have the intensity of the laser-pulse response imbedded in them, and as such they will have a better chance of showing certain detailed features that can be used to distinguish oils from one another.

The method of the present invention depends on the monitoring of the variations occurring in the shapes of the normalized time-resolved fluorescence spectra with respect to time. Contour diagrams constructed from these spectra are portrayed as fingerprints useful to identify oils without the need for further mathematical analysis, such as deducing the effective lifetimes.

The present invention makes it possible to distinguish the, different grades of crude oils, even if the excitation wavelength is not near 254 nm. An excitation wavelength at 355 nm, for example, can produce fingerprints capable of distinguishing blended crude oils of different commercial grades.

The fingerprints are also useful in the monitoring of the degradation of lubricant and transformer oils. And in another immediate application of the invention the oAPI gravity of crude oils can be directly estimated by analyzing the shapes of the time-resolved fluorescence spectra. (See Hegazi et al., above). (oAPI is the American Petroleum Institute gravity, which is one of the schemes by which crude oils are classified and is based on specific gravity values of the 250 to 275 C (1 atm) and the 275 to 300 C, (40 mm) distillation fractions.)

None of the above inventions and patents, taken either singularly or in combination, is seen to describe the instant invention as claimed. Thus a method for characterization of petroleum oils using normalized time-resolved fluorescence solving the aforementioned problems is desired.

SUMMARY OF THE INVENTION

When a crude oil sample is irradiated with a pulsed UV laser radiation it emits a bluish white light (referred to as fluorescence) that lasts for 20–50 ns after the end of the excitation pulse. If the laser pulse width is of the order of 10 ns then considerable overlap occurs between the temporal responses of the excitation and the fluorescence pulses. This invention is a method of obtaining useful temporal-spectral information about the crude oil without resorting to de-convolving the temporal response of the laser pulse from the resulting fluorescence signal. This is done by 1) measuring the excited fluorescence spectra at narrow time gates (TG's) of 2 or 5 ns within the temporal overlap region, 2) normalizing these time-resolved fluorescence spectra at a particular emission wavelength to highlight the shapes of their profiles, and then 3) comparing the changes in these shapes as function of time and wavelength simultaneously either by constructing contour diagrams (which present some sort of visual fingerprint) or by measuring areas under the curves of particular, emission regions.

The results depend on the shape of the laser pulse but not on its intensity, and therefore they would be universal if a laser, pulse of particular standard shape and a standard detection response were to be employed. To produce fingerprints of high. distinctive features, the wavelength of the excitation laser pulse should be at 266 nm or shorter so that the fluorescence spectra will include contributions from the light aromatic compounds. However, the method can still produce adequate fingerprints, but of less distinctive features, if longer wavelengths (i.e., 355 nm) are used, instead. In fact the ability to use the 355 nm wavelength for fingerprinting crude oils is one of the advantages of this method over the other time-resolved fluorescence methods.

Besides fingerprinting crude oils and their thermal distilled fractions, the invention can also be used to monitor the degradation of mineral oils, such as lubricants and transformer oils.

Accordingly, it is a principal object of the invention to provide a method for the characterization and fingerprinting of petroleum oils and other complex mixtures.

It is another object of the invention to provide a method as above based on time-resolved, laser-induced fluorescence spectroscopy.

It is a further object of the invention to provide a method as above which provides fingerprints of crude oils and other complex, mixtures without resorting to any kind of approximation.

Still another object of the invention is to provide a method as above capable of distinguishing between closely similar crude oils of the same grade.

Yet another object of the invention is to provide a method as above capable of estimating the oAPI gravity value of crude oils.

Still another object of the present invention as above capable of monitoring the degradation of mineral oils used in lubrication and transformers.

Yet another object of the invention is to provide a method as above depending on exciting the wavelength-resolved fluorescence of samples with ultraviolet pulsed laser radiation, measuring them at specific time gates within the temporal response of the excitation laser pulse, and comparing them in terms of their shapes alone, i.e., fingerprints.

It is an object of the invention to provide improved methods for the purposes described which are inexpensive, dependable and fully effective in accomplishing their intended purposes.

These and other objects of the present invention will become readily apparent upon further review of the following specification and drawings.

BRIEF DESCRIPTION OF THE DRAWINGS

FIG. 4A is a chart of lifetime decay curves of the time-resolved fluorescence signals of crude oils H and A when excited by 250 nm laser radiation and measured at the same emission wavelength of 420 nm.

FIG. 4B is a chart of lifetime decay curves of the time-resolved fluorescence signals of crude oil H when excited by 355 nm laser radiation and measured at two different emission wavelengths 400 nm and 460 nm.

FIGS. 5A through 5H are charts of time-resolved fluorescence spectra of crude oils H, N, A, and U, when measured at TG 0, 2, 4, and 8 (FIGS. 5E–5H) and at TG 0 and 8 (FIGS. 5A–5D), the spectra in FIGS. 5E–5H being plotted relative to each other in intensity while those in FIGS. 5A–5D are superimposed on each other with the intensities at 420 nm normalized to 1.

FIGS. 14A through 14D are charts of contours of equal fluorescence intensities of the non-normalized time-resolved. fluorescence spectra of FIG. 12 drawn as functions of wavelength and TG simultaneously.

FIGS. 15A and 15B are charts of contours of equal fluorescence intensities of the normalized time-resolved fluorescence spectra of Arabian Extra Light and Arabian Light drawn as functions of wavelength and TG simultaneously. Normalization wavelength was at 420 nm.

FIGS. 16A through 16C are charts of normalized time-resolved fluorescence spectra measured at TG 0 and TG 10 of the same lubricant oil when it was fresh, 5-week degraded, and 4-month degraded.

Similar reference characters denote corresponding features consistently throughout the attached drawings.

DETAILED DESCRIPTION OF THE PREFERRED EMBODIMENTS

The present invention is a method based on time-resolved laser-induced fluorescence spectroscopy for the characterization and fingerprinting of petroleum oils and other complex mixtures. The method depends on exciting the wavelength-resolved fluorescence spectra of samples using an ultraviolet pulsed laser radiation, measuring them at specific time gates within the temporal response of the excitation laser pulse, and comparing them in terms of their shapes alone without taking into account their relative intensities. The method has the advantage of providing fingerprints of crude oils and other complex mixtures without resorting to any kind of approximation, making it capable of distinguishing between closely similar crude oils of the same grade.

A detailed description of the method is presented in remote and non-remote setups, along with its applications in fingerprinting blended and non-blended crude oils using different ultraviolet excitation wavelengths. Applications on estimating the API gravity value of crude oils and monitoring the degradation of mineral oils used in lubrication and transformers are also described.

Apparatus and System

The system can be constructed to work in remote sensing as well as in non-remote sensing applications.

Figure 1:
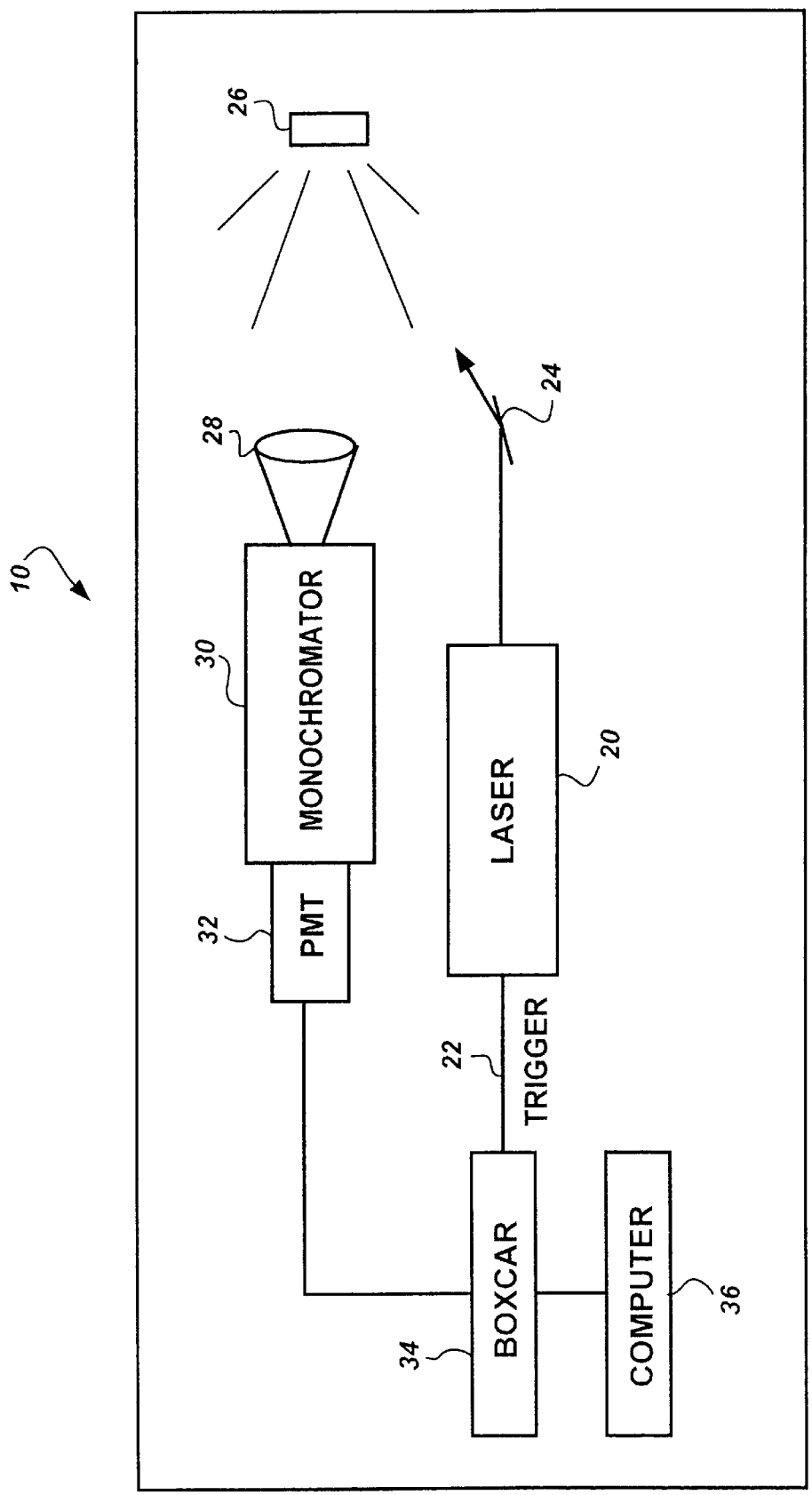
FIG. 1 is a schematic diagram for the non-remote experimental setup. The oil sample is held inside a quartz cuevette. The Boxcar is comprised of a signal processor coupled with a gated integrator. The laser is one that generates pulsed UV wavelength, such as a YAG laser, a YAG-pumped dye laser or YAG-pumped MOPO laser. The photomultiplier-monochromator-Boxcar combination can be replaced by an optical channel analyzer.

Referring to FIG. 1, non-remote system 10 includes pulsed UV, laser 20 having trigger 22, such as the fourth harmonic or the third harmonic of a Nd:YAG laser, a pumped pulsed dye laser, or a pumped pulsed MOPO laser irradiating, by means of mirror 24, an oil sample that is contained in a quartz cuevette 26. The resulting fluorescence signal from the oil is steered by proper quartz collecting lenses 28 onto the entrance slits of a medium-resolution, monochromator 30 for dispersion, after which it is detected by a, fast photo multiplier 32 mounted at the exit slits of the monochromator. The detected fluorescence signal is sent to a signal processor coupled with a gated integrator(Boxcar 34) and a PC computer 36 having monitor 38 for sampling and digitizing it according to specific time gates and time gate widths.

The system 10 depends on scanning the monochromator in the wavelength range from slightly longer than the laser excitation wavelength to 600 nm. Another possible setup would be to replace the monochromator/ photomultipier/ gated-processor combination with a gated optical multichannel analyzer to obtain instant time-resolved spectra without the need for the time-consuming scanning.

In the original experiments the following equipment were used: An f/3.4 Applied Photophysics monochromator, A Hamamatsu R1564U-07 photo multiplier, A EG&E Model 4402 signal processor coupled with a EG&E Model 4422 gated-integrator, and two different laser sources of pulse width of ~10 ns: Quanta-Ray GCR YAG laser (355 nm), Spectra Physics DRC YAG laser (355 nm). The former was used also to pump a Quanta-ray MOPO laser to get 250 nm and 225 nm output radiations, while the latter was used also to pump a Spectra Physics dye laser to get 280 nm output radiation. The pulse width of the MOPO output was ~8 ns. The slits of the monochromator were kept fixed at 1 mm, the scanning was done at a rate of 1.6 nm per second, the laser energy was maintained at ~5 mJ, and the time gate widths were chosen to be either 2 ns or 5 ns, where the peak of the laser pulse was chosen to be a reference point as explained in the next section.

Figure 2:
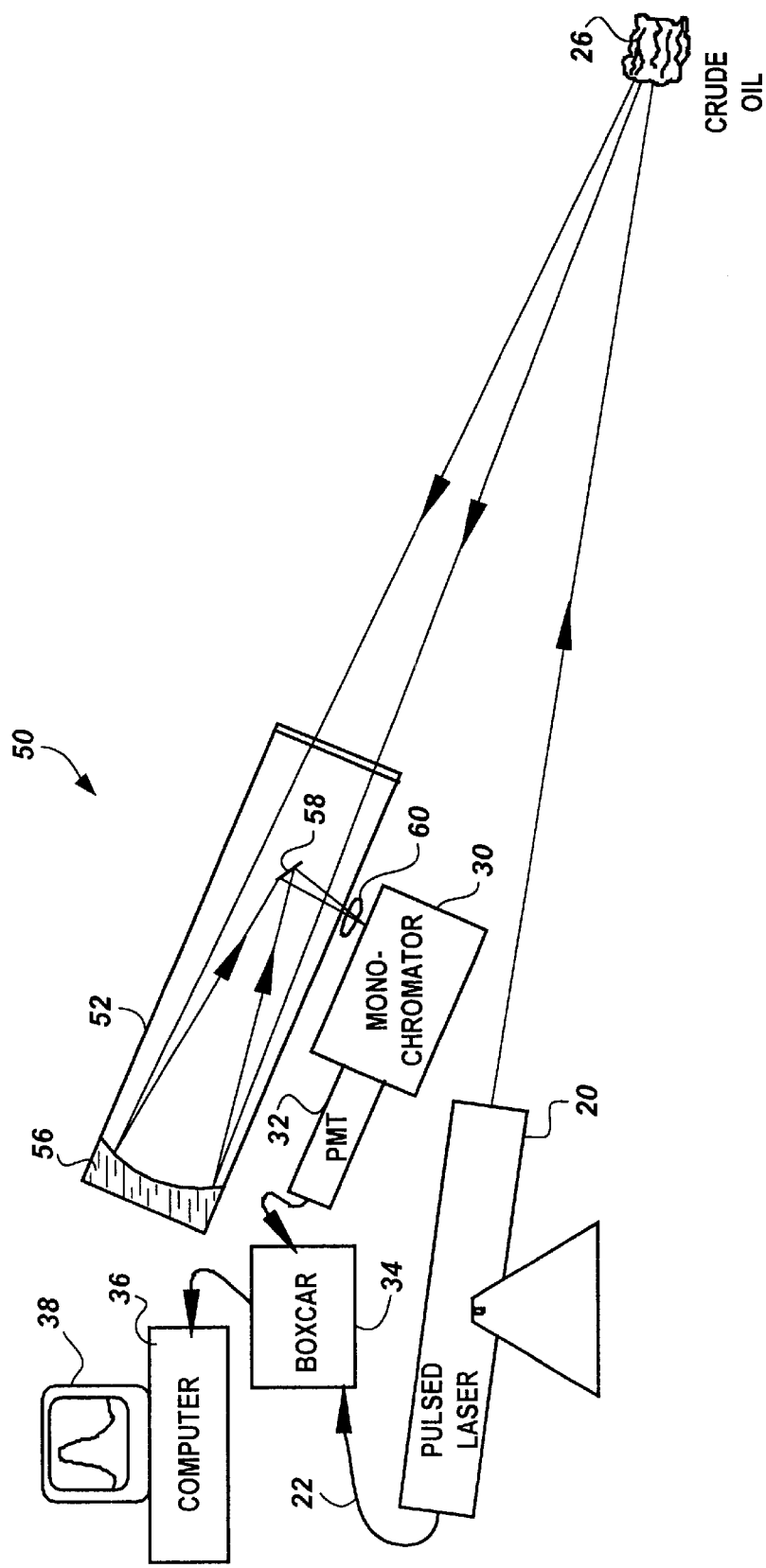
FIG. 2 is a schematic diagram for the remote experimental setup. The Boxcar, and the pulsed laser are described as in FIG. 1. The photomultiplier-monochromator-Boxcar combination can be replaced by an optical channel analyzer.

Referring to FIG. 2, the remote sensing system 50 includes a Newtonian telescope 52 having a having a concave mirror 56 and an image focal mirror 58 employed in place of the steering lenses of system 10. A lens and filter 60 is placed before the entrance slits of the monochromator 30 to cut off the back-scattered laser light. The signal processing system of FIG. 1, employing photomultiplier 32, Boxcar 34, computer 36, and 38, and the excitation system of FIG. 1, employing pulsed laser 20, trigger 22, and sample 26(the sample may be in-situ) serve similar functions in remote sensing system 50.

Sample and Data Analysis

To elucidate the measurement and data analysis procedures the following procedure using four non-blended crude oil samples is presented. The non-blended crude oils are all from Saudi Arabian fields but of different grades: Crude H (API=50.24, classified as Super Light grade), Crude N (API=39.33, classified as Extra Light grade), Crude A (API= 35.15, classified as Light grade), and Cruder U (API=30.71, classified as Medium grade). The experimental setup used is similar to the one shown in FIG. 1, with the laser operating at a wavelength of 250 nm from a Nd:YAG-pumped MOPO laser.

Figure 3A:
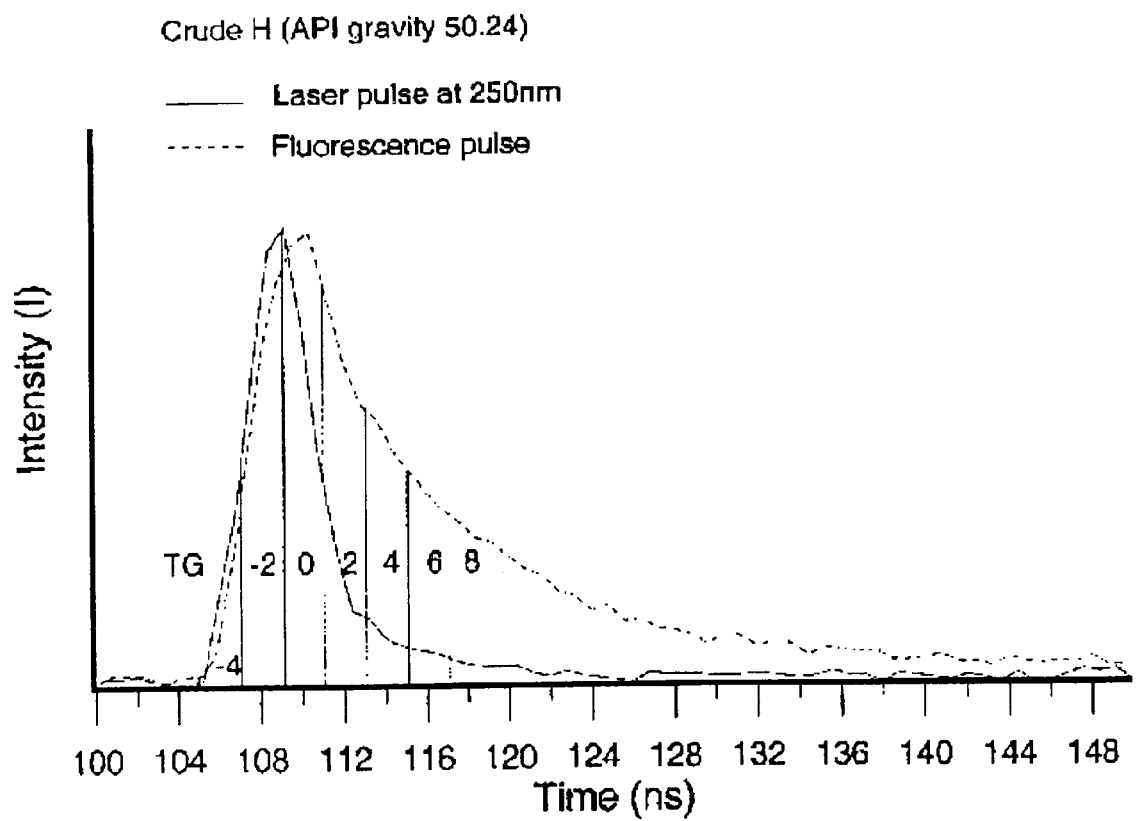
FIG. 3A is a chart showing temporal profiles of the excitation laser pulse at 250 nm (generated using a YAG-pumped MOPO laser) and the resulting crude H fluorescence pulse at 420 nm.

Referring to FIG. 3A, there are shown temporal profiles of the, excitation laser pulse at 250 nm (generated using a YAG-pumped MOPO laser) and the resulting crude H fluorescence pulse at 420 nm. The intensities of the pulses are not drawn relative to each other. The time gates (TG's) at which the fluorescence emission was measured are sketched schematically inside the fluorescence pulse. The FIG. 3B chart shows examples of how the shapes of the time-resolved fluorescence spectra become different when measured at three different TG's.

Figure 3B:
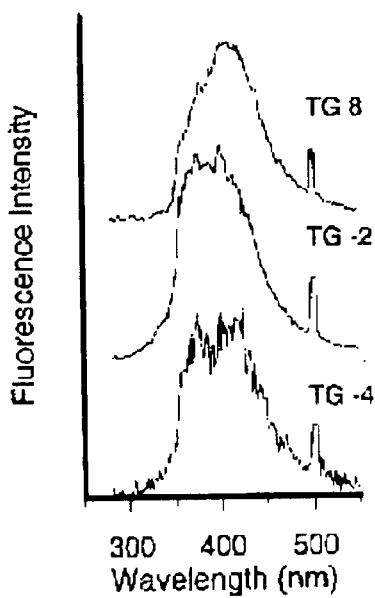
FIG. 3B is a chart showing examples of how the shapes of the time-resolved fluorescence spectra become different when measured at three different TG's.

FIG. 3A shows the temporal responses of the laser pulse at 250 nm, the resulting fluorescence pulse at 420 nm from crude H, and how the time gates at which the fluorescence spectra are measured are chosen. The time gates (TG's) are marked here as 0, 2, 4, etc., to easily identify the left edge of each TG. For example, TG 0 is a time-gate of 2-ns width beginning exactly at the peak of the laser-pulse, TG 2 is a time-gate of 2-ns width beginning 2 ns after the peak of the laser pulse, and so on. Notice that TG at −2 and −4 are located within the leading edge of the laser pulse, and that the reference point of the TG's is chosen to be the time corresponding to the peak of the laser pulse intensity. The FIG. 3B depicts traces of the time resolved frequency(TRF) spectra of crude H measured at three of these TG's, i.e., −4, −2, and 8, which illustrate how the shapes of the TRF spectra vary at different TG's. These variations will be different for different crude oils and will be used here to construct unique fingerprints for them.

For comparison purposes, it is useful to show how the temporal decay curves of the resulting fluorescence signals vary with respect to both wavelength and type of oil.

Referring to FIGS. 4A and 4B, there are shown lifetime decay curves (FIG. 4A) of the time-resolved fluorescence signals of crude oils H and A when excited by 250 nm laser radiation and measured at the same emission wavelength of 420 nm, and lifetime decay curves (FIG. 4B) of the time-resolved fluorescence signals of crude oil H when excited by 355 nm laser radiation and measured at two different emission wavelengths 400 nm and 460 nm, respectively. It is clear that, in each case, these decay curves are different from one another and that they are not simple exponential functions. This is due to the complex nature of the crude oils and also due to the convolution from the laser pulse itself. The only available non-convolved part of the fluorescence temporal profile occurs right after the end of the laser pulse, which, in principle, could be used for straight lifetime measurements. However, the intensity there is less than 10% of the intensity at the middle of the laser-pulse interval, making it impractical for remote sensing measurements.

In the present method no analysis is carried out on the time decay curves, but rather on the "shapes" of the time-resolved fluorescence spectra.

Referring to FIG. 5A–5H, complete sets of the resulting time-resolved spectra of these four oils are shown. Time-resolved fluorescence spectra are shown of crude oils H, N, A, and U, when measured at TG 0, 2, 4, and 8 (FIGS. 5E–5H), and at TG 0 and 8 (FIGS. 5A–5D). The spectra in FIGS. 5E–5H are plotted relative to each other in intensity, while those in FIGS. 5A–5D are superimposed on each other with the intensities at 420 nm normalized to 1. The truncated peaks at 500 nm correspond to the second order of the 250 nm excitation laser radiation. (Spectra of TG −2 and TG 6) are not shown)

In FIGS. 5E–5H, the TRF spectra measured along the trailing edge of the laser pulse, in particular TG 0, 2, 4, and 8, are plotted in accordance to their relative intensities. It can be seen that, for each crude oil, the drop in the intensities of the TRF spectra is not the same at different wavelengths. These, intensity drops are expected to map the lifetime decay curves of the crude oil when measured at the corresponding wavelengths. The fluorescence intensities at the 420-nm emission wavelength of crude oil H, for example, appear to drop more or less following the fluorescence lifetime decay curve shown FIG. 4A. Therefore, if contour diagrams of the fluorescence intensities are constructed based on the TRF spectra that are plotted in FIGS. 5E–FH, then they will simply not produce any additional information other than showing an overall picture of the lifetime decays at all wavelengths.

In the present method the contour diagrams are not constructed in such a manner. They are constructed in a way that takes into account the shapes of the TRF spectra alone and not their relative intensities. To do so the intensity of each TRF spectrum must first be normalized at a particular wavelength. The choice of this wavelength is arbitrary and it must remain unchanged for all the time-resolved spectra. The FIGS. 5A–5D show how two of the spectra: TG 0 and TG 8 of the four crude oils for example, appear relative to each other when they are normalized at 420 nm. By doing such normalization, the spectra become different in "shape" only and not in "shape+intensity".

Inventive Sample Fingerprinting and Error Analysis

By normalizing all the time-resolved spectra and plotting them in contours as functions of wavelength and time-gate simultaneously, another type of diagram will emerge.

Referring to FIGS. 6A–6D there is shown the type of contour diagram constructed by this procedure, which illustrates the inventive method of fingerprinting oils and other complex mixtures. Contours of equal fluorescence intensities of the time-resolved fluorescence spectra of FIGS. 5A–5D are drawn as functions of wavelength and TG simultaneously. The contour lines reflect the variations in the shapes of the time-resolved fluorescence spectra only and not their relative intensities. FIGS. 6A–6D are just a, different way of highlighting the temporal-spectral information that are already included in the time resolved fluorescence spectral of FIG. 5A–5D.

Without normalization, i.e., without excluding the relative intensities of these spectra, the contour diagrams would resemble one another making them useless in oil identification, especially when the UV excitation wavelength is longer than 300 nm. This is demonstrated below when the results of an experimental precedure done with excitation wavelength of 355 nm is presented. It should also be clear that the charts FIGS. 6A–6D are not the only possible way for representing the data.

By choosing a different wavelength for normalizing the intensities of the spectra, the contour patterns will be different in shape. However, but they will still retain differences between them that can be used as additional pieces of information in the oil identification process. Instead of identifying an oil sampler by a single fingerprint, it is now possible to identify it by a set of fingerprints, each of which is constructed at a different normalization wavelength.

Although, all of these fingerprints stem from the same temporal-spectral data of the oil's fluorescence spectra, the availability of such a number of them will definitely minimize the chances of making mistakes in its identification, since the whole process depends on comparing patterns of fingerprints in a visually manner. This is an advantage that does not exist in the images produced by the present gated CCD and streak cameras, which produce digitized images that contain both shapes and intensities of the time-resolved fluorescence spectra.

When plotting the time-resolved spectra in terms of contour lines a certain standard should be taken into account otherwise there will be no basis on which the comparison can be made. Because the contour lines represent normalized intensities of the fluorescence spectra, the two important parameters that should be standardized in the contouring process are the zero intensity level and the increment between the intensity levels. All contour diagrams should start with the same intensity level, e.g., 0.0, and all should have contour lines that represent intensities incremented in the same constant step. In FIGS. 6A–6D(above), for example, the contour lines represent intensity levels incremented in steps of 0.05 of the normalized intensities at 420 nm. The smaller the step the more features will appear in the contour diagrams and the higher the resolution of the fingerprints will be. However, there is always a limit for the lowest increment to be used below which the features would be meaningless. This limit depends on the uncertainty of the shapes of the time-resolved fluorescence spectra themselves.

The uncertainty in the shapes of the spectra in FIGS. 5A–5D(above) are due to two experimental factors. The first is the uncertainty in choosing the time gate in the gated integrator, which in this case was ±200 ps. The effect of this uncertainty on the overall shapes of the spectra depends on where the time gate is chosen; steeper parts of the temporal response of the fluorescence signal will produce slightly higher uncertainty in the shapes of the corresponding time-resolved fluorescence spectra than the flatter parts. We estimate that the uncertainty in the ratio $I_{600nm}/I_{400nm}$ of the spectra in FIGS. 5A–5D due to the ±200 ps uncertainty ranges between 2–5%.

The second experimental factor affecting the spectra is the resolution of the monochromator and its scanning speed. This factor, in addition to digital (random) noise, is responsible for the wiggles appearing on these spectra, but it has no effect on the overall shapes of the spectra. In the experiment leading to the spectra of FIGS. 5A–5D, the monochromator slits were fixed at 1 mm giving rise to a spectral resolution of about 0.1 to 0.2 nm, but because the interest was to record rapidly the overall shapes of the spectra the collection of the data points was done every 1.6 nm instead, and this in turn gave rise to the wiggles seen in the spectra. The lowest increment that can be used when contouring the normalized intensities is limited to this latter type of uncertainty. We estimate that the lowest increment that could be used in FIGS. 6A–6D ranges between 0.02 and 0.03 of the normalized intensity at 420 nm of the TG 0 spectra. In other words, there is still more room in the contours of FIG. 6A–6D to show finer details.

These contour diagrams can be used as fingerprints by considering certain features in them. For example, the diagrams of FIGS. 6A–6D(above) show that there is a general trend in the patterns between 350 nm and 450 nm., i.e., that the higher the crude grade the more the high-levels (e.g., 1, 0.95, 0.85) extend toward later times without becoming interrupted. See for example how the innermost contour of crude H, which is level 1, encircles a larger area than that of crude N, and how the 0.95 contour of crude N is larger than that of crude A, and so on. Another feature can also be noticed at 350 nm where the contours become more congested as the grade of the crude increases. (The features appearing at 500 nm do not represent meaningful data in these diagrams since they are due to the second order of the laser excitation wavelength).

Referring to FIGS. 7A–7D, there are shown contours of equal fluorescence intensities of the time-resolved fluorescence spectra of FIGS. 5E–5H(above) when normalized at 450 nm revealing another fingerprint for each of the crude oils constructed by normalizing the fluorescence intensities at 450 nm instead of 420 nm. In this case the intensities at 450 nm become the base on which the variations in the shapes of the time-resolved fluorescence spectra are displayed. This has the effect of straightening up the contour lines at 450 nm (instead of at 420 nm), which will be at the expense of the shapes of the contour lines at other wavelengths. The end result will be contour diagrams that are slightly different from those of FIGS. 6A–6D, respectively. Notice that the diagrams in FIGS. 7A–7D still maintain general features that change in some trend with respect to the oil grade.

The shapes of the normalized fluorescence spectra, themselves, depend upon the shape of the excitation laser pulse and also on the spectral response of the detection system. Therefore universal fingerprints of each type of crude oil would be possible only if these two elements are standardized.

Theoretical Considerations of Results

The UV-induced fluorescence of crude oils is due to hundreds of different compounds, many of which are aromatic. The composition of the fluorescing compounds in crude oils, their concentrations, and the factors influencing the fluorescence quenching such as heavy elements, water contents, etc., all contribute to the overall shapes of the resulting fluorescence spectra. If no time sampling is taken into account, i.e., if the fluorescence spectra of crude oils are measured within a broad time window that covers the whole lifetime span of the fluorescence signal, then the shapes of the fluorescence spectra of different crude oils will basically be identical with no distinct features that can be used to distinguish the crude oils from one another.

Figure 8:
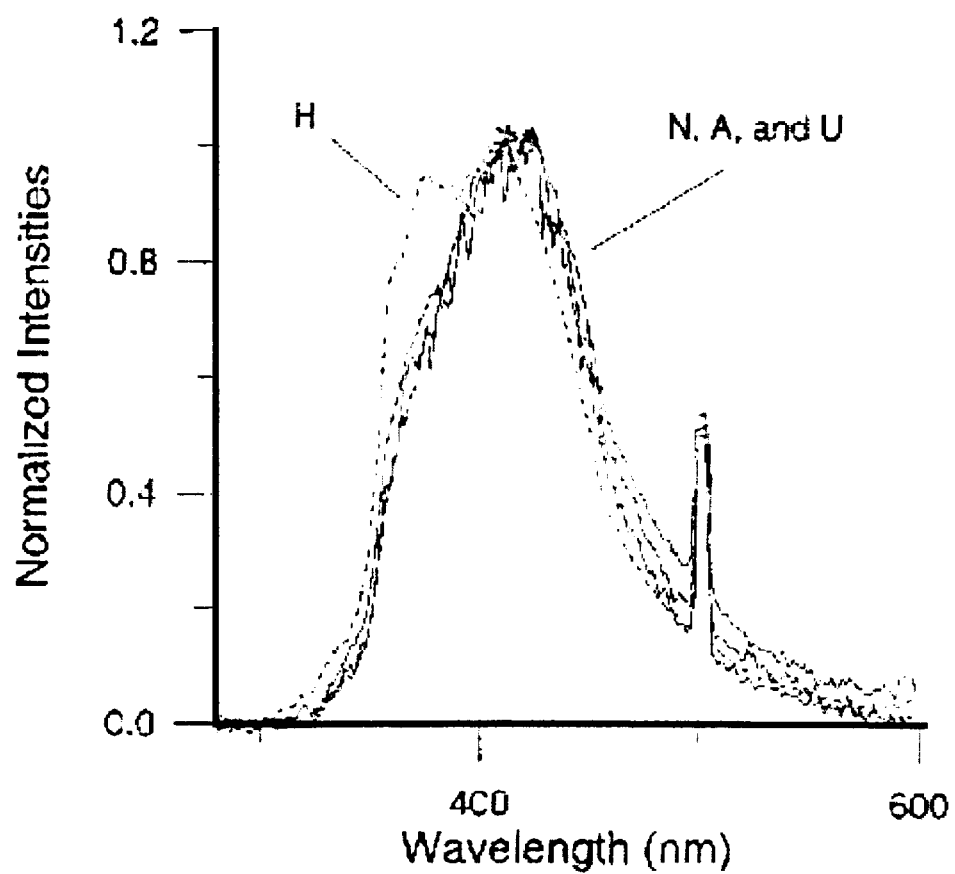
FIG. 8 is a chart of fluorescence spectra of crude oils H, N, A, and U when excited by pulsed 250 nm laser radiation measured with a wide time gate width(GW) of 20 ns.

Referring to FIG. 8, there are shown fluorescence spectra of crude oils H, N, A, and U when excited by pulsed 250 nm laser radiation. The spectra were measured with a wide time gate width (20 ns), which covered most of the resulting fluorescence time. The spectra shows featureless structures and cannot be used for characterization purposes. The fluorescence spectra of the H, N, A, and U crude oils were excited by the same laser pulse as that of FIGS. 3A and 3B, and were measured with a time gate window of 20 ns. It can be seen that, with the exception of the case of Super Light grade, it is practically impossible to use these spectra to distinguish the other three grades from each other.

If time sampling is considered, the resulting time-resolved fluorescence spectra will reflect the composition of the fluorescing compounds in terms of how their lifetimes fit within the particular time gates that are chosen. Consider that a mixture is made of two compounds A and B that become excited by a radiation of wavelength and that the two compounds fluoresce accordingly ink more or less the same broad wavelength range but in two different band shapes. Suppose also that the fluorescence lifetimes of these two compounds are different and that the excitation wavelength is pulsed with a certain pulse shape, say as that shown in FIG. 3A(above). If two time-resolved fluorescence spectra of the mixture are measured at two consecutive 2 ns time gates within the laser pulse, say TG 0 and TG 2 of FIGS. 3A and 3B, then they will definitely be different in shape because the intensity of the laser pulse is not constant from TG 0 to TG 2. In TG 2, the resulting fluorescence will be from the immediate contribution of compounds A and B plus the contribution from these two compounds that had already started at higher intensity in TG 0 and had arrived at TG 2 after suffering some decays in intensity according to the compounds' effective lifetimes. When measured at a particular time gate the time-resolved fluorescence spectra will always have a contribution from the immediate excitation of the fluorescence at this time gate plus a contribution from the excitation of the fluorescence that occurred prior to that time gate.

In the case of complex mixtures, such as crude oils, the time-resolved fluorescence spectra will be due to hundreds of such compounds that have different spectral and temporal characteristics, and following the same reasoning, their time-resolved fluorescence spectra will also vary in shape relative to the time gate. Therefore, within this context, it is simply a matter of investigating how the shapes of these time-resolved fluorescence spectra change with respect to time gates to be able to distinguish the different types of crude oil from one another.

Using the above line of reasoning, the total fluorescence intensity $I^{tot}$ of a crude oil, at a particular wavelength $\lambda$, with respect to time can then be described as proportional to the sum of two quantities. One is due to the fluorescence occurring within a particular 2 ns gate-width and the other quantity is due to the fluorescence that was initiated at earlier time. In a mathematical form $I_\lambda^{tot}(t)$ can be written as follows:

$$I_\lambda^{tot}(t) \propto L(t) I_{k\lambda}(0) + \Sigma_k [\int_0^t L(t') I_{k\lambda}(t-t') dt']$$ [1]

where the subscript k refers to any specie capable of fluorescing at wavelength $\lambda$, whether excited directly by the laser pulse or, through other relaxation or energy transfer processes, L(t) is the laser pulse intensity at time sampling point t, and $I_{k\lambda}(0)$ is the fluorescence intensity at wavelength $\lambda$ due to that specie, which occurs within the 2 ns temporal gate-width(clearly, the narrower the gate width (GW) the more accurate this description will be). $I_{k\lambda}(t-t')$ is the fluorescence intensity due to specie "k" that was excited at earlier time t'<t (this latter intensity is different from $I_{k\lambda}(0)$ because it encounts a decay according to some exponential function). In equation 1, the summation is over all the species that can fluoresce at the particular wavelength $\lambda$, and the integration limits are from the beginning of the laser pulse t'=0 (i.e., the left edge of the laser pulse), to t'=t (i.e., the beginning of the 2-ns GW), and the detection time response is considered constant for the sake of simplicity.

Equation 1 describes the fluorescence intensity at one emission wavelength only. The rest of the emission wavelengths throughout the fluorescence spectrum will also have their own time-dependent equations, giving rise to the sort of variations observed along the wavelength range of the fluorescence spectrum as seen in FIGS. 5A–5H(above). The factor responsible for these changes is the second term on the left-hand side of Equation 1. In other words, if only the first term were present in Eq. 1, then the fluorescence spectra measured at different time gates would be identical in shape, and would differ only in their relative intensities.

EXAMPLE 1

Procedure to Estimate the API of Crude Oils Using the Shapes of the Time-Resolved Fluorescence Spectra By analyzing the shapes of the time-resolved fluorescence spectra it is also possible to estimate the API values of crude oil(See Hegazi et al. "Estimation of Crude Oil grade Using Time Resolved Fluorescence Spectra) (Accepted for publication 2002). This can be done by measuring ratios of certain areas under the curves of these spectra and plotting them as functions of API value. The following experiment elaborates on such a procedure.

In this experimental procedure, time-resolved fluorescence, spectra of two more non-blended crude oils from the eastern part of Saudi Arabia, crude K (API=28.48, classified as Heavy grade) and crude B (API=24.00, classified as Heavy grade), were excited under the exact experimental conditions that lead to the results of FIGS. 5A–5H (above) for the H, N, A, and U crude oils, and the time-resolved fluorescence spectra of all the six crude oils were then analyzed to find if there is a correlation between certain features of the spectra and the oAPI value.

The analysis of the complete set of time-resolved fluorescence spectra revealed that the region between 300 and 390 nm of the spectra are more sensitive to the oil grade than the rest of the, spectral region, and that the earlier the time gate they are measured at the more accurate the estimation would be for the oAPI value of crude oils.

Figure 9:
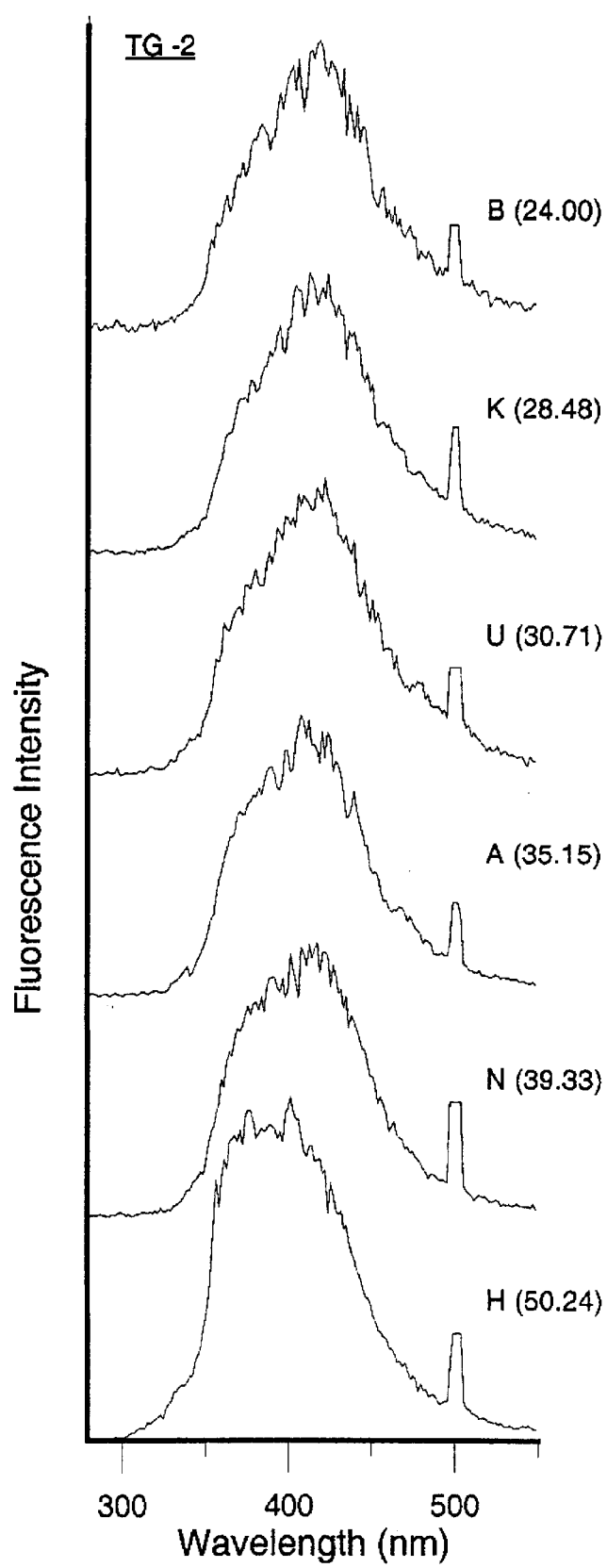
FIG. 9 is a chart of time-resolved fluorescence spectra of the six crude oils when measured at TG −2. The values of their API gravity are quoted inside brackets.

Referring to FIG. 9, there are shown time-resolved fluorescence spectra of the six crude oils when measured at TG −2. The values of their oAPI gravity are quoted inside brackets. FIG. 9 depicts the time-resolved fluorescence spectra of all six crude oils when measured at TG −2. It is clear that shoulders appearing at about 380 nm represent an interesting feature that changes systematically with respect to °API value—the higher the grade (i.e., the higher the °API value) the more prominent the shoulder becomes. These shoulders were found to diminish gradually when the spectra were measured at later TG's.

Figure 10A:
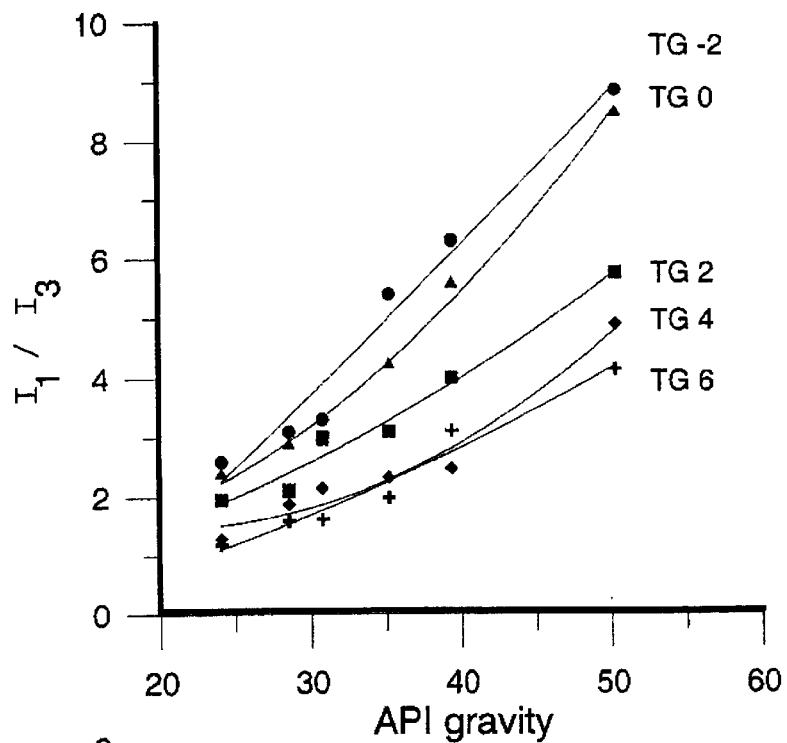
FIGS. 10A and 10B are charts of ratios of area under the curve between 355 and 390 nm ($I_1$) to area under the curve between 432 and 480 nm ($I_2$), and to area under the curve between 480 and 545 nm ($I_3$), respectively in the time-resolved fluorescence spectra of FIG. 9 as functions of API gravity. (Closed circles represent data from the TG −2 spectra, triangles from the TG 0, squares from the TG 2, diamonds from the TG 4, and pluses from the TG 6 spectra.)
Figure 10B:
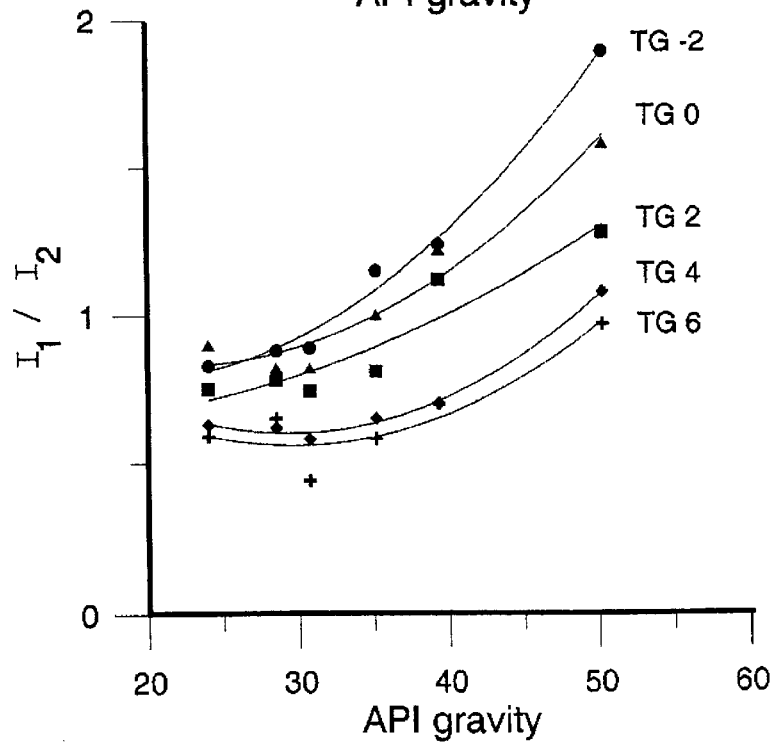

Referring to FIGS. 10A and 10B, there are plotted ratios of area under the curve between 355 and 390 nm ($I_1$) to area under the curve between 432 and 480 nm ($I_2$) (FIG. 10B), and to area under the curve between 480 and 545 nm ($I_3$) (FIG. 10A), in the time-resolved fluorescence spectra of FIG. 9 as functions of °API gravity. Closed circles represents data from the TG −2 spectra, triangles from the TG 0, squares from the TG 2, diamonds from the TG 4, and pluses from the TG 6 spectra.

Both plots (FIGS. 10A and 10B) demonstrate this effect as they show ratios of area under the curve between 355 and 390 nm ($I_1$) to area under the curve between 432 and 480 nm ($I_2$), and to area under the curve between 480 and 545 nm ($I_3$), as functions of API gravity. These ratios are plotted in five different symbols corresponding to the five different TG's that were used. The solid lines represent polynomial fits of second order for each TG data. The second-order polynomial fit is chosen arbitrarily at this point and should be re-evaluated when data from a large number of crude samples become available. The fitted curves demonstrate clearly the significance of the choice of TG on the resolution ability between crude oils of close °API values.

At earlier TG's the curves become steeper, which means that the tolerance in the calculation of °API values from a given $I_1/I_2$ or $I_1/I_3$ ratio is smaller at earlier TG's than at later TG's. These plots, prepared for a trained set of data, can be used as conversion curves by which the °API values can be read immediately in terms of the measured time-resolved fluorescence spectra. The accuracy of such conversion curves apparently will depend on the quality of the signal-to-noise ratios of the time-resolved fluorescence spectra. However, since there are great differences in oil compositions from one region to another, one should expect also that the accuracy of these conversion curves would be higher if they are constructed for crude oils obtained from the same geographical region, than if they are obtained from different regions.

A clue as to which aromatic compounds, in particular, are responsible for the fluorescence near the 380-nm wavelength can be determined by consulting the data on their fluorescence spectra(See I. B. Berlman, "Handbook of fluorescence spectra of aromatic compounds, second edition, Academic Press, New York (1971)). These aromatic compounds happen to be in the C14–C18 range, which may include benzo (e)pyrene, pyrene, anthracene, and 9-methylanthracene (See Taylor et al. "Excitation Resolved Synchronous Fluorescence Analysis of Aromatic Compounds and Fuel Oil." Analytical Chemistry, vol. 59 pp. 2180–2187 (1987)). Note that there are also numerous nitrogen-bonded aromatic compounds, whose fluorescence spectra peak at about 380 nm, however, these compounds are expected to be in trace amounts in crude oils and should not have appreciable effect on the overall fluorescence spectra.

It is commonly known that high-grade crude oils usually contain higher yields of light aromatics (and lower yields of heavy aromatics) than low-grade crude oils. This can be verified by volume measurements of thermally distilled fractions. Using the ASTM D285 method(See Annual Book of ASTM Standards, Section 5, Volume 05.01, (1984)), p. 162, D 285), we distilled 300 mL of each of crude oils H, N, A, U, and K and measured the volumes of the resulting fractions in temperature ranges of 0–100 C, 100–105 C, 105–140 C, 140–200 C, and 200 C-end point. It was found that, in general, the volumes of low-temperature distillates (up to 200 C degree) increase with the increase of °API gravity, while the reverse is true for the distillates of the last fraction and also for the residues that could not be recovered from the distillation process. These different yields have a major bearing on the shapes of the fluorescence spectra, since usually the lighter aromatic compounds fluoresce at shorter wavelengths than do the heavier compounds, as we confirmed by examining the excited fluorescence spectra of the distilled fractions.

Figures 5A, 5B, 5C, 5D:
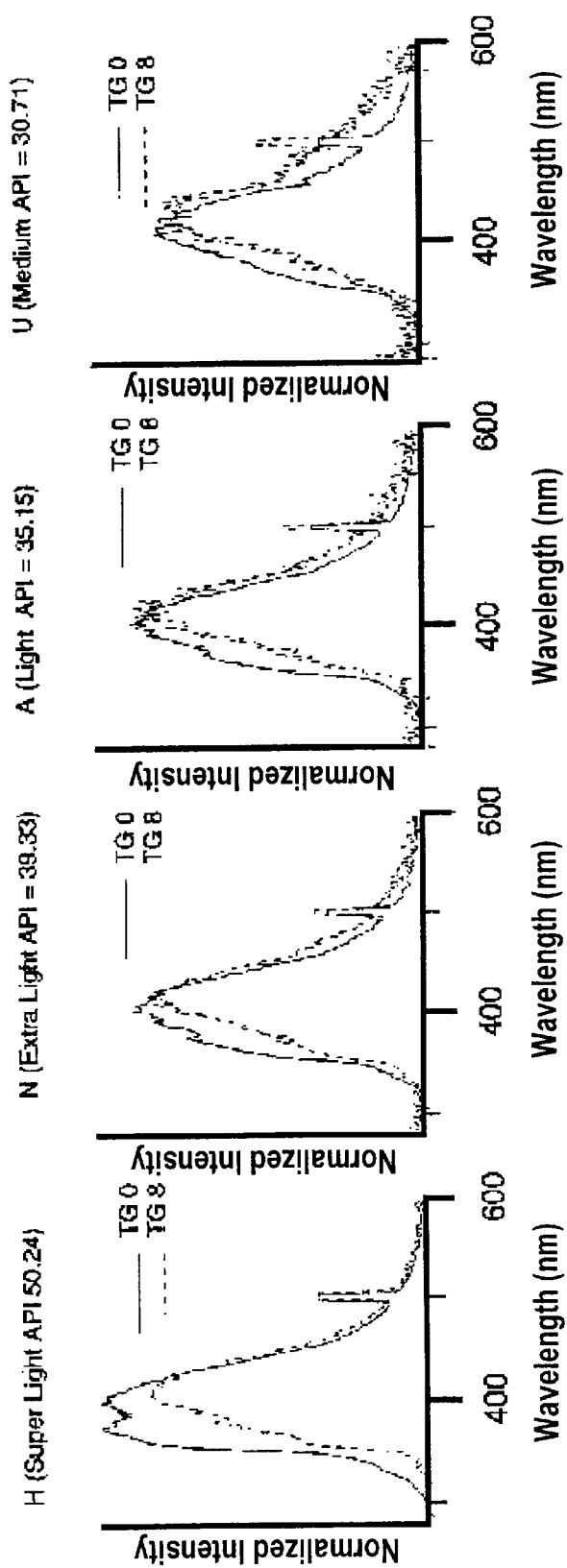
Figures 6A, 6B, 6C, 6D:
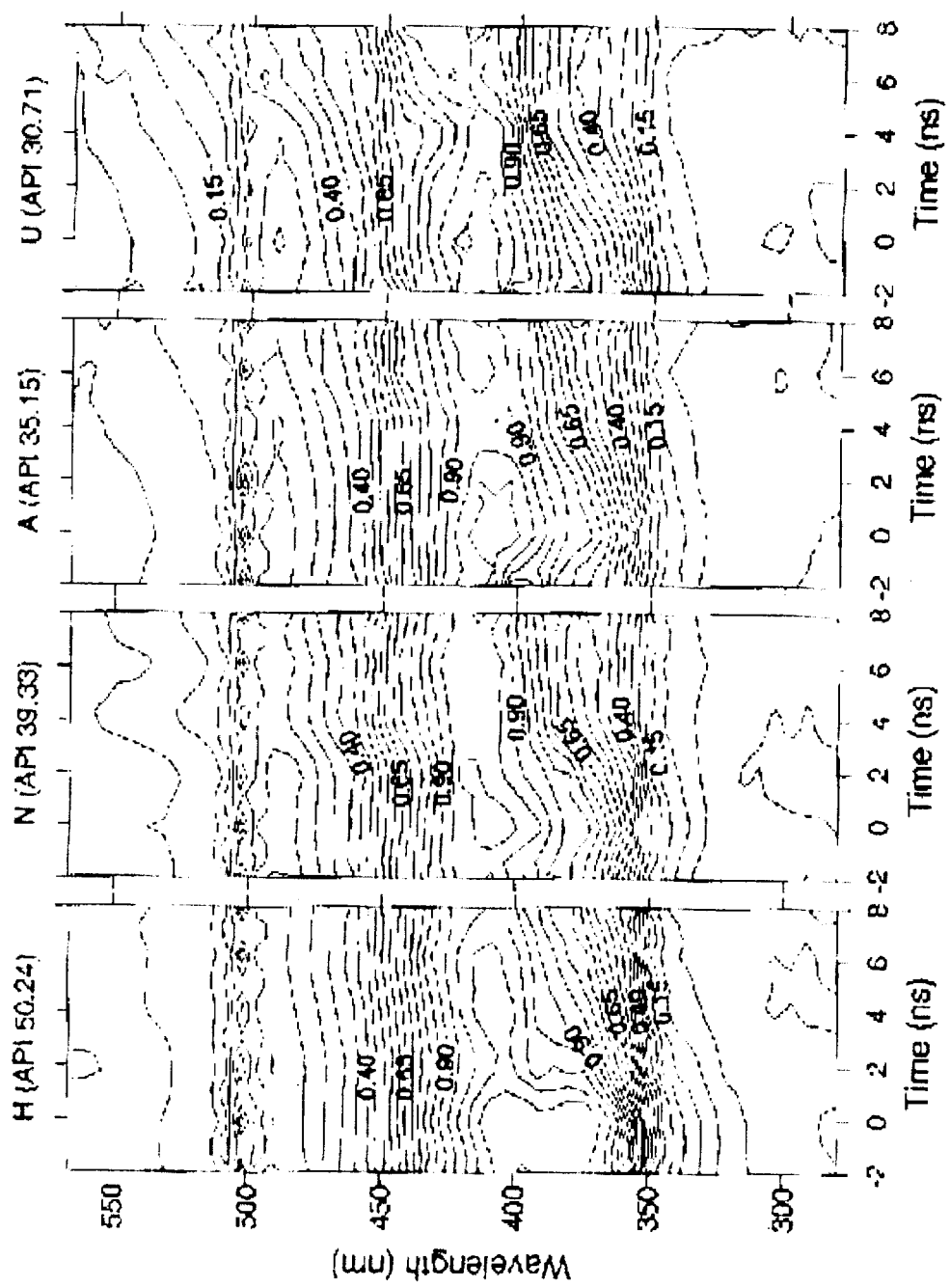
FIGS. 6A through 6D are charts of contours of equal fluorescence intensities of the time-resolved fluorescence spectra of FIGS. 5A–5D drawn as functions of wavelength and TG simultaneously when normalized at 420 nm.
Figures 7A, 7B, 7C, 7D:
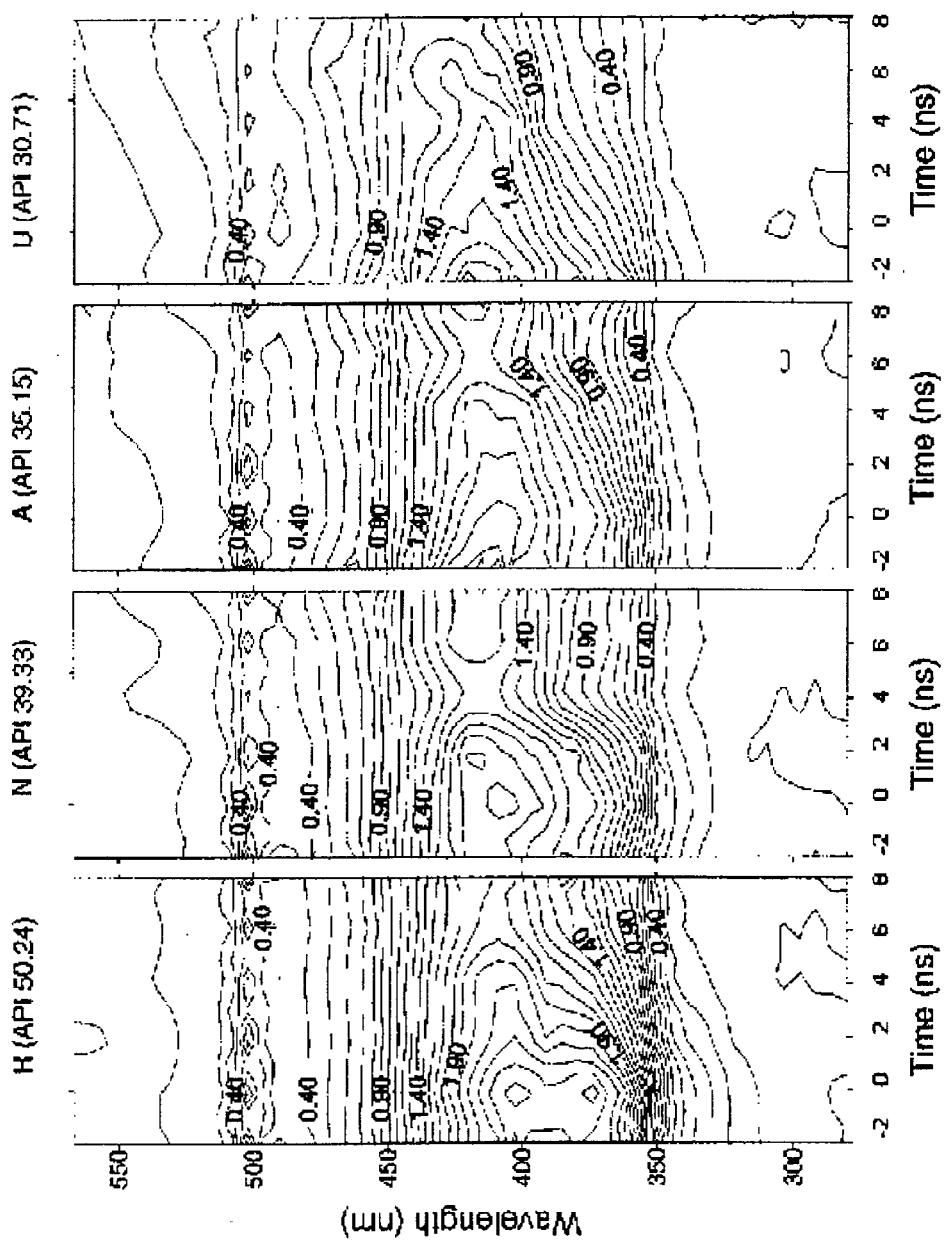
FIGS. 7A through 7D are charts illustrating contours of equal fluorescence intensities of the time-resolved fluorescence spectra of FIGS. 5A–5D when normalized at 450 nm.

This explains why the maximum intensities of the time-resolved fluorescence spectra in FIGS. 5A and 5B(above) shift in a gradual manner toward longer wavelengths as we go from higher-grade to lower-grade crude oils. It also explains the results relating the shoulder at 380 nm to °API gravity on the basis that the concentration of C14–C18 aromatic compounds must be higher in high-grade crude oils than in low-grade ones.

The dependence of the 380-nm shoulder on TG, on the other hand, has to do with the fluorescence lifetimes of the compounds. At later time gates(TG's), the time-resolved fluorescence spectra include not only the immediate fluorescence occurring within the time frame of the particular TG but also fluorescence that had been excited at earlier times, from the start of the laser pulse until the left edge of the TG. The fluorescence signals coming from these earlier times contribute to the measured time-resolved fluorescence intensity in amounts that depend on the lifetimes of the fluorescing species, the shape of the laser pulse, and the particular position of the TG. The closer the 2-ns TG is to the laser left edge the closer the resemblance of the excitation pulse would be to a delta-function, which would produce minimum earlier-time effect. Apparently, the shoulder at 380 nm is significantly influenced by this effect since it washes out gradually with time.

By using the synchronous scan fluorescence technique a similar trend in the intensity of the shoulder at 380 nm can also be found. Based on this trend, Shen et al., above, reported that the synchronous scan fluorescence spectra could be used in practice to distinguish high-grade from low-grade Arabian crude oils.

EXAMPLE 2

Fingerprinting of Marketed (Blended) Crude Oils Using Excitation Wavelength of 355 nm Marketed crude oils are usually prepared as blends of assorted virgin crude oils extracted from different separate wells, and combined in certain proportions to produce products of specific chemical and physical properties. Because of this blending, however, the differences between the fluorescence spectra of the final products diminish as compared to those between the original virgin crude oils, making it harder to distinguish blended crude oils from each other than to distinguish virgin crude oils from each other on the basis of any fluorescence technique. The situation becomes worse if, on top of that, an excitation wavelength unsuitable to excite the light aromatic compounds is used.

In the following experimental procedure these conditions are challenged using the method introduced in this invention to show the advantage of this technique over the other available time-resolved fluorescence techniques. The marketed crude oils considered here are the Saudi Arabian blends and the excitation wavelength used is the third harmonic of the YAG laser at 355 nm. The advantage of this wavelength is that it can be easily produced at high intensity, using the third harmonic of the YAG laser, which makes it attractive for remote sensing applications (The conversion factor of the fundamental wavelength of the YAG to 355 nm is about three times more than that of the fundamental to 266 nm). Its disadvantage is that it is not suitable for the excitation of the light aromatic compounds of the crude oils, which are usually key compounds that determine the crude oil grades. Hence, the distinguishing ability between the crude oils will have to depend thoroughly on the differences in the fluorescence spectra displayed by the heavier aromatic compounds.

The experiment addresses also the difference between contour diagrams constructed from normalized time-resolved fluorescence spectra and those constructed from non-normalized time-resolved fluorescence spectra, i.e., those that involve the relative intensities of the time-resolved fluorescence spectra to explain the improvement in the distinguishing ability our method offers. The blends used in this work are four of the marketed crude oils of Saudi Arabia, i.e., Arabian Extra Light (AEL), Arabian Light (AL), Arabian Medium (AM), and Arabian Heavy (AH). AEL is a blend produced from the fields of Berri and Shaybah, the latter of which is located in the Empty-Quarter desert. AL is a blend from the fields of Abqaiq, Uthmaniyah, Abu Hadriyah, and Hawiyah, AM is a blend from the fields of Marjan, Zuluf, Abu Safah, and Khurasaniyah, and finally AH is a blend from different wells of the vast field of Safaniah, the largest offshore oil field in the world. The general properties of these blends are listed in Table 1, below.

TABLE I

General Properties of Marketed Arabian Crude Oils

| Test | Method (ASTM #) | AEL | AL | AM | AH |
|---|---|---|---|---|---|
| Gravity °API | D287 | 38.7 | 34.0 | 30.5 | 28.1 |
| Ash, ppm | D482 | 20 | 44 | 58 | 110 |
| Pour pt. C | D97 | −17.8 | −15.0 | −12.2 | −23.2 |
| Sediment & water | D96 | Tr. | Tr. | Tr. | Tr. |
| Sulphur, % wt | D129 | 1.10 | 1.81 | 2.59 | 3.35 |
| C residue, % wt | D189 | 2.0 | 3.58 | 5.87 | 7.53 |
| Vanadium, ppm | | 3 | 15 | 28 | 69 |
| Nickel, ppm | | 1 | 3 | 8 | 21 |
| Nitrogen, % wt | | 0.04 | 0.10 | 0.12 | 0.16 |

AEL: Arabian Extra Light
AL: Arabian Light
AM: Arabian Medium
AH: Arabian Heavy

The experimental setup was the same as that shown in FIG. 1(above), but with excitation wavelength taken directly from the third harmonic output of a Quanta-Ray GCR Nd:YAG laser at 355 nm. The shape of the laser pulse in this case is different from that shown in FIG. 3A(above), because it did not pass through the crystals and the other optical paths that are present inside the MOPO laser.

Figure 11A:
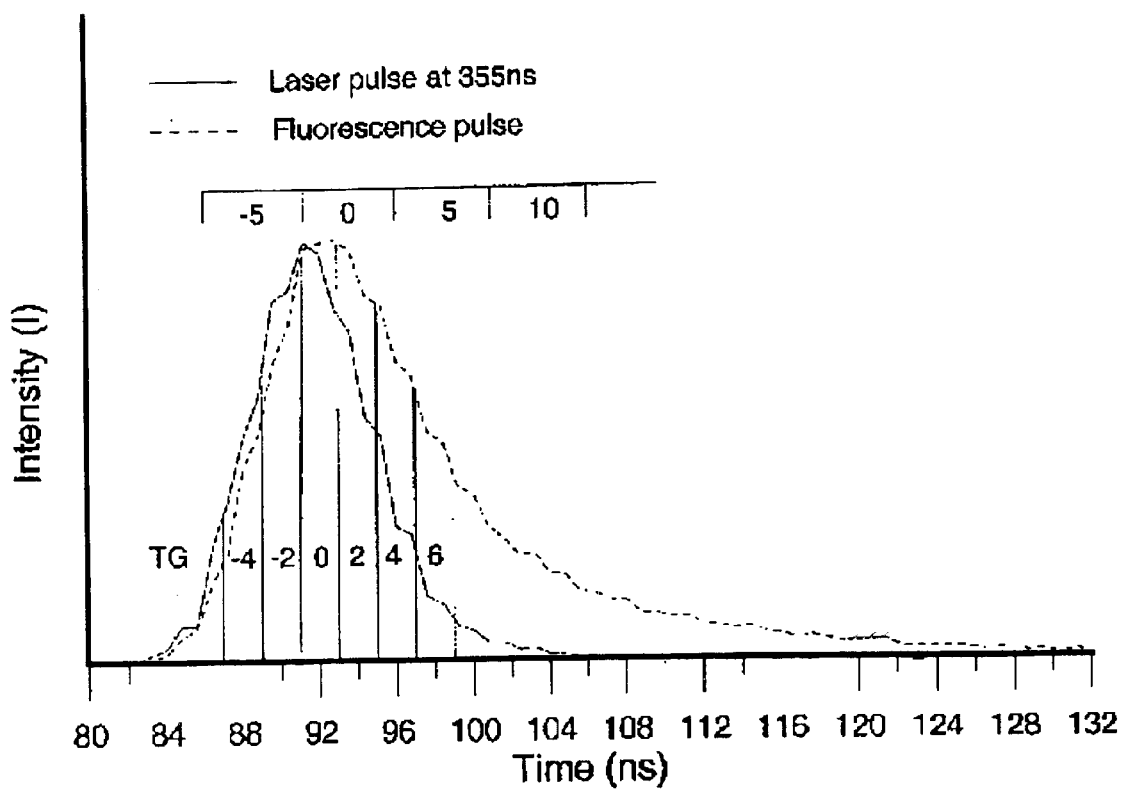
FIG. 11A is a chart depicting temporal profiles of the excitation laser pulse at 355 nm and the resulting crude H fluorescence pulse at 420 nm, the 2-ns time gates (TG's) at which the fluorescence emission was measured being sketched schematically inside the fluorescence pulse, while those of the 5-ns TG's are drawn on top.
Figure 11B:
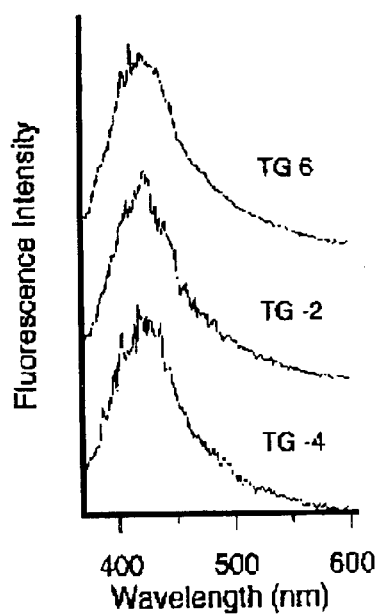
FIG. 11B is a chart showing examples of how the shapes of the time-resolved fluorescence spectra become different when measured at three different TG's.
Figure 12A:
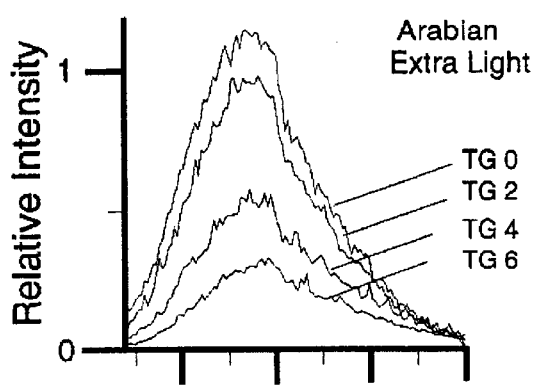
FIGS. 12A through 12D are charts of time-resolved fluorescence spectra of the marketed Arabian crude oils when excited by 355-nm wavelength and measured at TG 0, 2, 4, and 6 plotted relative to each other in intensity.
Figure 12B:
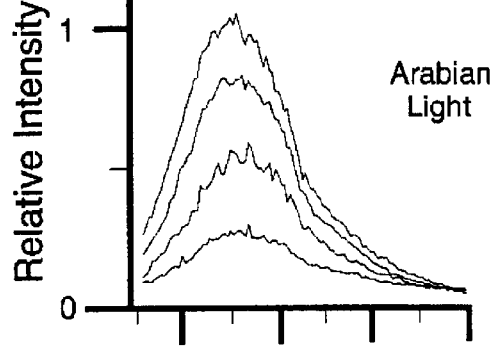
Figure 12C:
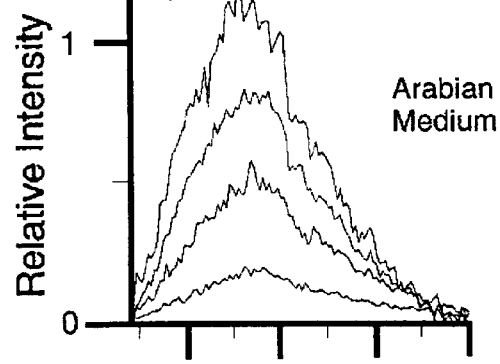
Figure 12D:
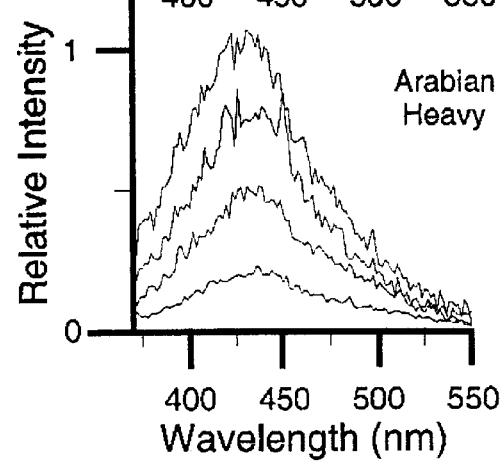
Figures 13A, 13B, 13C, 13D:
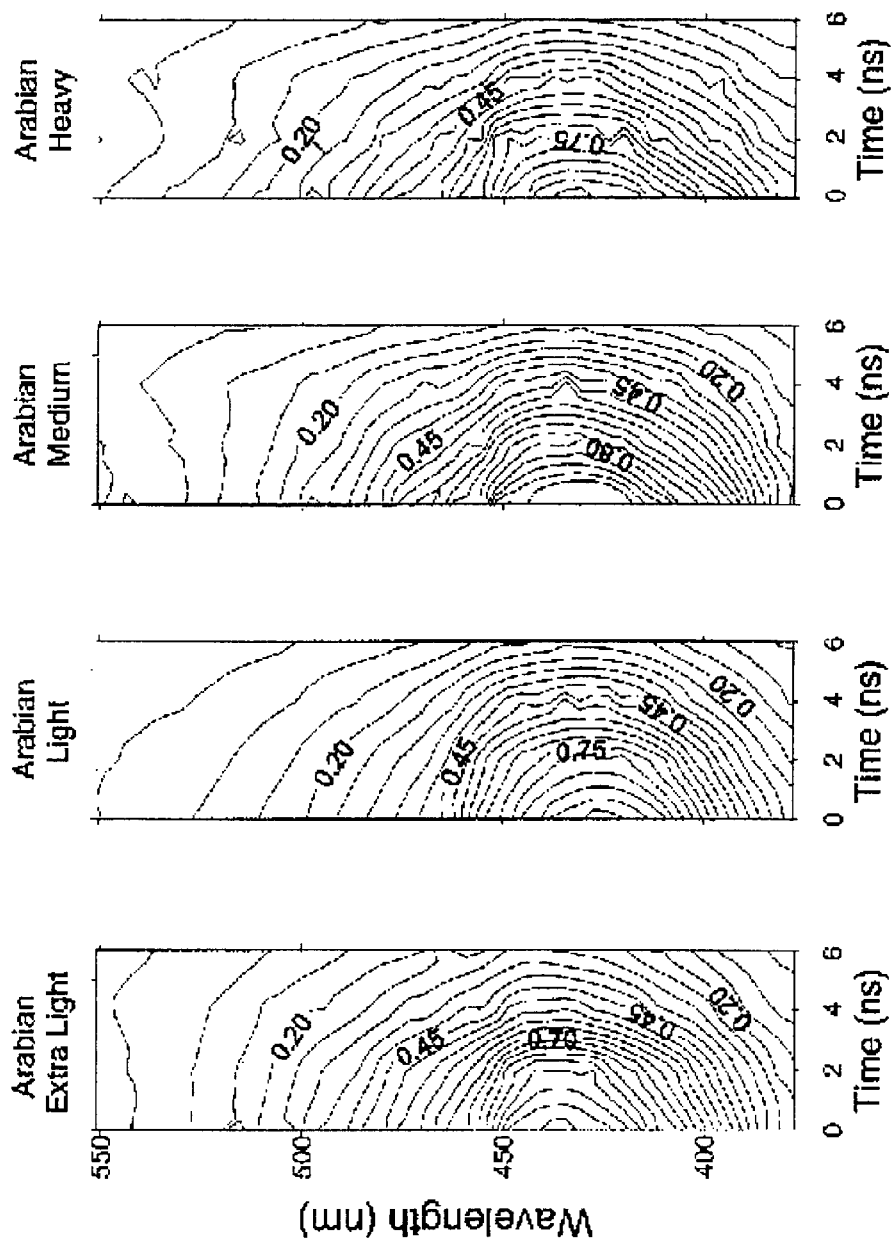
FIGS. 13A through 13D are charts of contours of equal fluorescence intensities of the time-resolved fluorescence spectra of FIGS. 12A–12D drawn as functions of wavelength and TG simultaneously.

Referring to FIG. 11A, temporal profiles are shown of the excitation laser pulse at 355 nm (generated using a the third harmonic output of a YAG laser) and the resulting crude H fluorescence pulse at 420 nm. The intensities of the pulses are not drawn relative to each other. The 2-ns time gates (TG's) at which the fluorescence emission was measured are sketched schematically inside the fluorescence pulse, while those of the 5-ns TG's are drawn on top. The FIG. 11B shows examples of how the shapes of the time-resolved fluorescence spectra become different when measured at three different TG's. FIG. 11A shows the temporal responses of this laser pulse and the associated fluorescence signal from crude H. The figure shows also the way the time gates of 2-ns and 5-ns widths are distributed following the same condition of using the maximum intensity of the laser pulse as a reference point. In the same nomenclature as above, the time gates are marked here as TG−2, TG 0, TG 2, TG 4, etc. for the 2 ns-width case, and as TG−5, TG 0, TG 5, TG 10, etc. for the 5 ns-width case, to easily associate them with the time intervals between their left edges and the reference point.

The FIG. 11B shows typical time-resolved fluorescence spectra of crude H at three different 2-ns time gates when excited by the 355-nm wavelength. It is clear that, although the shoulders near 380 nm no longer present when the excitation wavelength is at 355 nm, the time-resolved fluorescence spectra still display different shapes when measured at different time gates. The idea now is to show that these shape variations are adequate enough to identify the marketed crude oils.

The time-resolved fluorescence spectra of the marketed Arabian crude oil blends, excited by 355-nm wavelength and sampled at 2-ns, gate widths are plotted according to their relative intensities in FIGS. 12A–12D(below).

Referring to FIGS. 12A–12D, there are shown time-resolved fluorescence spectra of the marketed Arabian crude oils when excited by 355-nm wavelength and measured at TG 0, 2, 4, and 6. The spectra are plotted relative to each other in intensity. (Spectra of TG −2 are not shown)

If these relative intensities are taken into account when constructing the contour diagrams as explained above then the resulting contours will inherit the convolution of the laser pulse, and will not prove useful in distinguishing between the crude oils, especially now when the excitation wavelength is not suitable to excite the light aromatic compounds. This situation is depicted in FIGS. 13A–13D (below) for the four Arabian marketed crude oils.

Referring to FIGS. 13A–13D, there are shown contours of equal fluorescence intensities of the time-resolved fluorescence spectral of respective FIGS. 12A–12D drawn as functions of wavelength and TG simultaneously. The contour lines reflect the variations in the shapes of the time-resolved fluorescence spectra as well as in their relative intensities. Excitation wavelength is 355 nm. These diagrams represent, in contour fashion, what a gated streak camera or other multi-detector system would display in digital images. It can be seen that these diagrams are almost identical and that they clearly cannot be used for identification purposes. If only the shapes are considered in the contour diagrams then the situation becomes enhanced remarkably as shown in respective FIGS. 14A–14D(below).

Referring to FIGS. 14A–14D, there are shown contours of equal fluorescence intensities of the normalized time-resolved fluorescence spectra of respective FIGS. 12A–12D drawn as functions of wavelength and TG simultaneously. These contour lines reflect the variations in the shapes of the time-resolved fluorescence spectra, only, and not their relative intensities. Normalization wavelength was at 500 nm. Excitation wavelength was 355 nm. The wavelength at which the normalization was done in these diagrams was 500 nm. Unlike those of FIGS. 13A–13D(above), the contour diagrams of respective FIGS. 14A–14D reveal patterns that are remarkably different from one another, particularly for the Heavy, Medium, and Light grades. These patterns also show a clear trend that relates to the oil grade. This can be seen in the region between 400 nm and 470 nm, which describes a pattern of closed: contours in the Arabian Heavy case that open up and elongate in a gradual manner as we move toward the lighter Arabian grades.

As explained above, the contour patterns depend on the wavelength at which the time-resolved fluorescence spectra are normalized, and if a different wavelength is chosen whole new patterns will result. To produce patterns that can distinguish between widely different grades, it was found that the best wavelength at which the normalization of the spectra should be is at the long-wavelength end of the fluorescence spectrum, e.g., 500 nm, as demonstrated in FIG. 14, in which the resulting contour patterns are capable of distinguishing between the Heavy, the Medium, and the Light grades. The contour patterns of the Light and Extra Light grades, however, cannot be effectively distinguished from each other using this pattern representation. For this purpose, a different choice for the normalization. wavelength was tried. A logical choice was a shorter wavelength so that the differences in the short-wavelength end of the fluorescence spectra would be highlighted. This part of the spectrum is due to the lightest aromatic compounds that can be excited by the 355-nm laser wavelength as see FIGS. 15A and 15B(below).

Referring to FIGS. 15A and 15B, there are shown contours of equal fluorescence intensities of the normalized time-resolved fluorescence spectra of Arabian Extra Light and Arabian Light drawn as functions of wavelength and TG simultaneously. The contour lines reflect the variations in the shapes of the time-resolved fluorescence spectra only and not their relative intensities. Normalization wavelength was 420 nm. FIGS. 15A and 15B show the contour diagrams of the Arabian Extra Light and the Arabian Light blends, respectively, drawn after the intensities of their time-resolved fluorescence spectra had been normalized at 420 nm instead of 500 nm. The patterns here appear to be more different from each other than before, indicating that the crude oils are different. Contours of more profound differences in this particular case could be obtained of course if the excitation wavelength was shorter than 355 nm.

EXAMPLE 3

Using the Normalized Time-Resolved Fluorescence Spectra to Monitor the Degradation of Lubricant and Transformer Oils:

The above-described inventive technique may be applied to monitor the degradation of refined oils, such as lubricant and transformer oils. This is advantageous over other analytical electrical, or mechanical methods since the present fluorescence method can be performed without sample preparation.

The difference between crude oils and lubricants (or transformer oils) is that the latter represent basically a certain thermal cut of the crude oil that is mixed with certain additives to serve as oxidation inhibitors. It is shown that the final products do fluoresce when excited by UV radiation and that the, shapes of the time-resolved fluorescence spectra of the fresh and the degraded oils vary in different manners. A car-engine lubricant (Fuchs Super GT 20W/50) was chosen to investigate the degradation time-resolved fluorescence properties. The samples considered here were (1) fresh, (2) 5-week degraded, and (3) 4-month degraded samples, and their time-resolved fluorescence spectra were excited and measured using the experimental setup of FIG.1 (above). The excitation wavelength was at 280 nm, produced by a YAG-pumped dye laser whose pulse shape was similar to the one shown in FIG. 11(above). The TG's were chosen with widths of 5 ns instead of 2 ns with results shown in FIG. 16(below).

Referring to FIGS. 16A–16C, there are shown normalized time-resolved fluorescence spectra measured at TG 0 and TG 10 of the same lubricant oil when it was fresh, 5-week degraded, and 4-month degraded, respectively. The spectra were normalized at 450 nm. Excitation wavelength was at 280 nm. (Spectra of TG −5, 5, and 15 are not shown). The resulting normalized time-resolved fluorescence spectra at TG 0 and TG 10 are shown in FIGS. 16A–16C), where the normalization wavelength was chosen to be at 450 nm. It is clear that the spectra at these two time gates vary in shape in different manners depending on the ageing status of the lube oil. By considering the normalized spectra of the other time gates and comparing certain areas under their curves it is possible to construct conversion curves similar to those presented in FIGS. 10A and 10B(above) to predict the ageing of the oil quantitatively. In this case the x-axis would be the effective usage-time of the lubricant oil instead of the ○API value, and a trained set of data at several ageing times would be needed to construct a significant conversion curve.

It is also possible to predict the ageing of the oils in a qualitative manner using contour diagrams as described above.

Figures 17A, 17B, 17C:
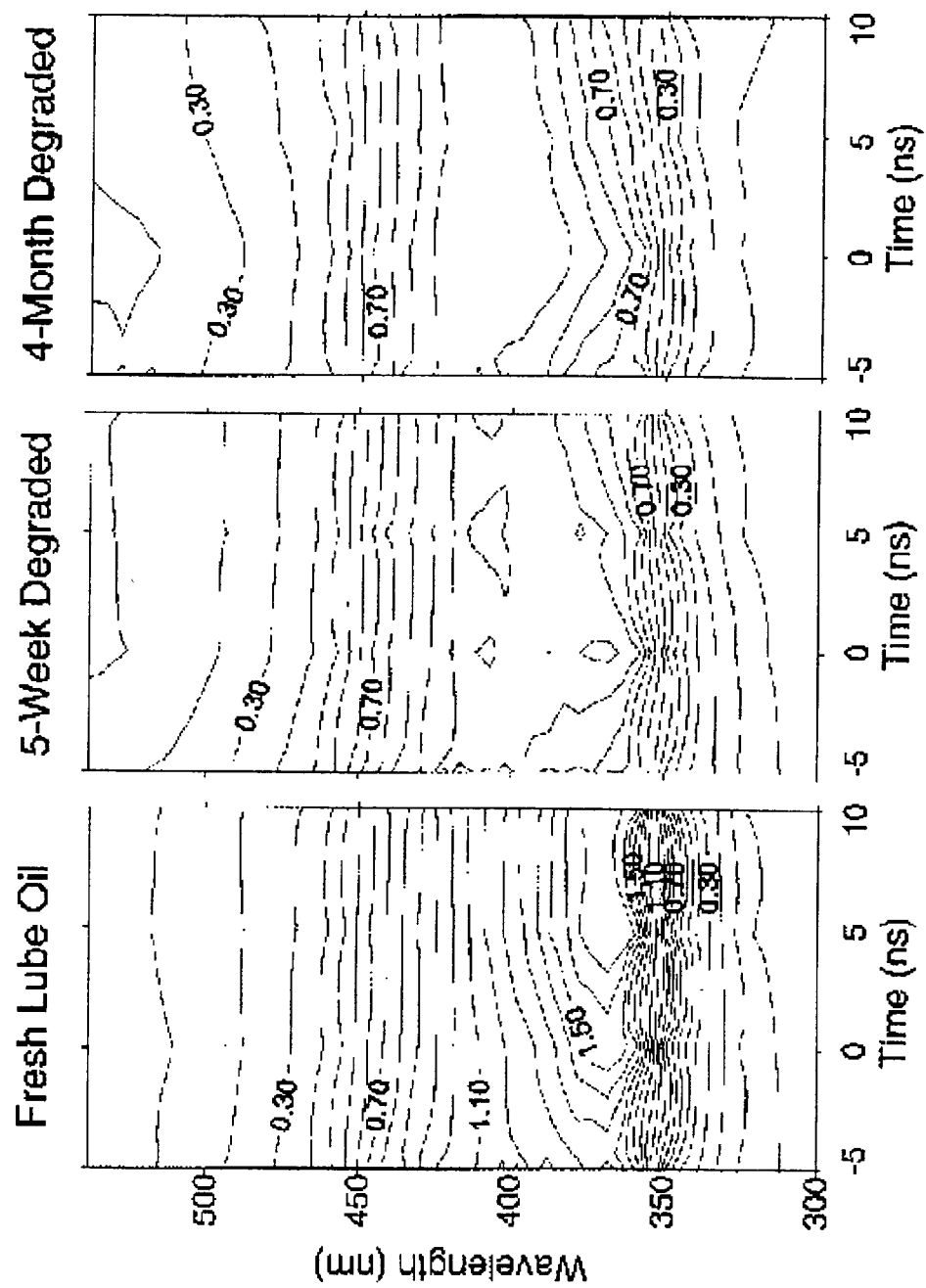
FIGS. 17A through 17C are contours of equal fluorescence intensities of the normalized time-resolved fluorescence spectra of the lubricant oil in the three ageing cases. Normalization wavelength was at 450 nm.

Referring to FIGS. 17A–17C there are shown contours of equal fluorescence intensities of the normalized time-resolved fluorescence spectra of the lubricant oil in the three ageing cases(above), respectively. The contour lines reflect the variations in the shapes of the time-resolved fluorescence spectral only and not their relative intensities. Normalization wavelength. was 450 nm.

A comparison between these diagrams show that there is al general trend in the contour patterns near 350 nm and also in the region between 350 nm and 430 nm, which change gradually with respect to the ageing status of the oil. As the oil age the contour lines between 330 and 370 nm become less congested, and the contour lines of higher intensity level, e.g., 1.10 and 1.50, start to disappear in the area between 350 and 430 nm. The diagrams in FIGS. 17A–17C show only the degradation at three ageing times, and, if a trained set of data is produced at different ageing times, then it would be possible to use it in predicting when the ageing oil needs to be replaced by fresh oil.

It is to be understood that the present invention is not limited to the embodiments described above, but encompasses any and all embodiments within the scope of the following claims.

We claim:

1. A method for characterization of petroleum oils using normalized time-resolved fluorescence comprising the following steps:

exposing an unknown petroleum oil sample to a pulse of ultraviolet laser radiation;

measuring the intensities of resulting fluorescence over the spectrum of wavelengths of light from said petroleum oil sample at specific narrow time gates within the temporal response of said laser pulse to form a time-resolved spectrum;

normalizing said time-resolved spectrum at a particular emission wavelength;

plotting said time-resolved spectrum in contours as functions of wavelength and time simultaneously;

comparing the resultant plots of said plotting step with those of known samples; and characterizing said unknown sample based on similarity of said resultant plots with those of a particular known sample.

2. The method of characterization of claim 1, wherein said time is determined relative to the maximum temporal response of said laser pulse.

3. The method of characterization of claim 2, wherein said time gate is from about 2 nanoseconds to about 5 nanoseconds in width.

4. The method of characterization of claim 3, wherein a monochromator is employed having slits in said intensity measuring step are fixed at 1 millimeter and scanned by a scanner/photomultiplier at a rate of 1.6 nanometers per second.

5. The method of characterization of claim 2, wherein said pulse of laser radiation is shorter than or equal to 266 nm in wavelength and said normalizing wavelength is 420 nm.

6. The method of characterization of claim 8, wherein said pulse of laser radiation is about 8 nanoseconds.

7. The method of characterization of claim 6, wherein said sample is crude oil.

8. The method of characterization of claim 2, wherein said sample is a blend of crude oils.

9. The method of characterization of claim 1, wherein said sample is non-remote.

10. The method of characterization of claim 1, wherein said sample is remotely located.

11. The method of characterization of claim 1, wherein said unknown sample plots are prepared for a plurality of laser excitation wavelengths.

12. A method for monitoring the degradation over time petroleum lubricants and transformer oils using normalized time-resolved fluorescence comprising the following steps:

exposing an unknown petroleum lubricant or transformer oil sample to a pulse of ultraviolet laser radiation;

measuring the intensities of resulting fluorescence over the spectrum of wavelengths of light from said petroleum lubricant or transformer oil sample at specific narrow time gates within the temporal response of said laser pulse to form a time-resolved spectrum;

normalizing said time-resolved spectrum at a particular emission wavelength;

plotting said time-resolved spectrum in contours as functions of wavelength and time simultaneously;

comparing the resultant plots of said plotting step with those of similar samples taken at known levels of degradation; and characterizing said unknown sample based on similarity of said resultant plots with those of a particular known sample.

13. The method of claim 12 wherein said excitation wavelength is 280 nm, said time-gates have a width of 5 nanoseconds, and said time-resolved fluorescence spectra is normalized at 450 nm.

14. The method of claim 13 further comprising the steps of; plotting said time-resolved spectrum;

determining the ratio of the area under a first segment of said time-resolved spectrum to at least a second segment of said time-resolved spectrum; and determining the degradation of said sample by comparing said ratio to a plot of ratios as a function of effective usage time for known lubricating and transformer oils.

15. The method of claim 14, wherein said plot of ratios are a mathematical fit of known data points.

16. The method of claim 14, wherein said sample is remotely located.

17. A method for estimation of the oAPI gravity of crude oils using the shapes of time-resolved fluorescence spectra comprising the following steps:

exposing an unknown crude oil sample to a pulse of ultraviolet laser radiation;

measuring the intensity of resulting fluorescence over the spectrum of wavelengths of light from said crude oil sample at a specific narrow time gate within the temporal response of said laser pulse to form a time-resolved spectrum;

plotting said time-resolved spectrum;

determining the ratio of the area under a first segment off said time-resolved spectrum to at least a second segment of said time-resolved spectrum; and determining the oAPI gravity of said sample by comparing said ratio to a plot of ratios as a function of oAPI gravities for known crude oils.

18. The method of claim 17, wherein said plot of ratios are a second-order polynomial fit of known data points and said ratio is determined at a point of time after the initiation and before the peak of the temporal response of said laser pulse.

19. The method of claim 17, wherein said laser pulse is about 10 nanoseconds and said determination point is −2 nanoseconds relative to said peak.

20. The method of claim 17, wherein said sample is remotely located.

* * * * *